US011814674B2

(12) United States Patent
Ng

(10) Patent No.: US 11,814,674 B2
(45) Date of Patent: Nov. 14, 2023

(54) RANDOM AMPLIFICATION METHODS FOR EXTREMELY LOW INPUT NUCLEIC ACIDS

(71) Applicant: The U.S.A., as represented by the Secretary, Department of Health and Human Services, Bethesda, MD (US)

(72) Inventor: Fei Fan Ng, Decatur, GA (US)

(73) Assignee: The United States of America, as represented by the Secretary Department of Health and Human Services, Bethesda, MD (US)

( * ) Notice: Subject to any disclaimer, the term of this patent is extended or adjusted under 35 U.S.C. 154(b) by 238 days.

(21) Appl. No.: 16/965,856

(22) PCT Filed: Feb. 1, 2019

(86) PCT No.: PCT/US2019/016383

§ 371 (c)(1),
(2) Date: Jul. 29, 2020

(87) PCT Pub. No.: WO2019/152860

PCT Pub. Date: Aug. 8, 2019

(65) Prior Publication Data

US 2021/0054437 A1 Feb. 25, 2021

Related U.S. Application Data

(60) Provisional application No. 62/625,675, filed on Feb. 2, 2018.

(51) Int. Cl.
*C12Q 1/686* (2018.01)
*C12Q 1/6806* (2018.01)

(52) U.S. Cl.
CPC .......... *C12Q 1/686* (2013.01); *C12Q 1/6806* (2013.01)

(58) Field of Classification Search
None
See application file for complete search history.

(56) References Cited

U.S. PATENT DOCUMENTS

2004/0023207 A1 * 2/2004 Polansky ............ A61K 48/005 435/456

FOREIGN PATENT DOCUMENTS

WO WO 2015/027135 2/2015

OTHER PUBLICATIONS

Ng, et al. A Metagenomics and Case-Control Study To Identify Viruses Associated with Bovine Respiratory Disease. Journal of Virology 89(10): 5340-5349. (Year: 2015).*

Kabir, S. Evaluation and adaptation of molecular approaches for detection and characterization of viruses of the respiratory tract. Ph.D. dissertation, University of Westminster. (Year: 2011).*

Aliotta et al. Thermostable Bst DNA polymerase I lacks a 3'-5' proofreading exonuclease activity. Genetic Analysis: Biomolecular Engineering 12:185-195. (Year: 1996).*

Ashrafi et al., "Selective Control of Primer Usage in Multiplex One-Step Reverse Transcription PCR," *BMC Mol. Biol.*, vol. 10:113, 2009, 13 pp.

Bhargava et al., "Technical Variations in Low-Input RNA-seq Methodologies," *Sci. Rep.*, vol. 4:3678, 2014.

Blainey, "The Future is Now: Single-Cell Genomics of Bacteria and Archaea," *FEMS Microbiol. Rev.*, vol. 37:407-427, 2013.

Borgström et al., "Comparison of Whole Genome Amplification Techniques for Human Single Cell Exome," *PLoS One*, vol. 12:e0171566, 2017.

Clontech Laboratories, Inc., SMARTer® Ultra™ Low RNA Kit for Illumina® Sequencing User Manual, www.clontech.com/xxclt_ibcGetAttachment.jsp?cItemId=41709, 2013, 21 pp.

Dill et al., "Distinct Viral Lineages from Fish and Amphibians Reveal the Complex Evolutionary History of Hepadnaviruses," *J. Virol.*, vol. 90:7920-7933, 2016.

Enzo Life Sciences, "Bioarray™ Low-Input RNA Amplification and Biotin Labeling System," http://www.enzolifesciences.com/ENZ-42422/bioarray-low-input-ma-amplification-and-biotin-labeling-system, downloaded Jul. 27, 2017.

Froussard, "rPCR: A Powerful Tool for Random Amplification of Whole RNA Sequences," *Genome Res.*, vol. 2:185-190, 1993.

Gawad et al., "Single-cell Genome Sequencing: Current State of the Science," *Nat. Rev. Genet.*, vol. 17:175-188, 2017.

Grothues et al., "PCR Amplification of Megabase DNA with Tagged Random Primers (T-PCR)," *Nucl. Acids Res.*, vol. 21:1321-1322, 1993.

International Search Report and Written Opinion from PCT/US2019/016383, dated Apr. 25, 2019, 12 pages.

Lang et al., "A Comparison of RNA Amplification Techniques at Sub-Nanogram Input Concentration," *BMC Genom.*, vol. 10:326, 2009.

Lebedev et al., "Hot Start PCR with Heat-Activatable Primers: A Novel Approach for Improved PCR Performance," *Nucleic Acids Res.*, vol. 36:e131, 2008.

Nanostring, nCounter® Low RNA Input Kit Product Bulletin, 4 pp., Mar. 2017.

Nugen, "Ovation® RNA Amplification System V2," user guide, 33 pp., downloaded Jul. 28, 2017.

Qiagen, "Whole Genome Amplification—Overview", https://www.qiagen.com/us/resources/technologies/wga/overvew-on-wga/?Print=1, downloaded Jul. 21, 2017, 2 pp.

Ramsköld et al., "Full-Length mRNA-Seq from single cell levels of RNA and individual circulating tumor cells," *Nat. Biotech.*, vol. 30(8):777-782, 2012.

Shanker et al., "Evaluation of Commercially Available RNA Amplification Kits for RNA Sequencing Using Very Low Input Amounts of Total RNA," *J. Biomol. Tech.* vol. 26:4-18, 2015.

Sigma-Aldrich, "SeqPlex™ RNA Amplification Kit," Technical Bulletin, 2014.

Tariq et al., "Whole transcriptome RNAseq Analysis from Minute Amount of Total RNA," *Nucleic Acids Res.*, vol. 39(18):e120, 2011, 10 pp.

(Continued)

*Primary Examiner* — Samuel C Woolwine
(74) *Attorney, Agent, or Firm* — Klarquist Sparkman, LLP

(57) ABSTRACT

Methods for the rapid amplification of extremely low quantity nucleic acids in a sample are provided. The disclosed methods are capable of amplifying less than 1 pg of DNA and/or RNA from a biological sample using a single tube and one-step or two-step preparation.

27 Claims, 8 Drawing Sheets

Specification includes a Sequence Listing.

(56) References Cited

OTHER PUBLICATIONS

Trombetta et al., "Preparation of Single-Cell RNA-Seq Libraries for Next Generation Sequencing," *Curr. Protoc. Mol. Biol.*, vol. 107:4.22.1-4.22.17, 2015.

Wong et al., "Use of Tagged Random Hexamer Amplification (TRHA) to Close and Sequence Minute Quantities of DNA—Application to a 180 kb Plasmid Isolated from *Sphingomonas* F199," Nucl. Acids Res., vol. 24:3778-3783, 1996.

Zhou et al., "DNA Core Evaluation of SMARTer® Ultra™ Low RNA Kit for Illumina Sequencing," University of Missouri DNA Core Facility, Mar. 2014.

* cited by examiner

RANDOM AMPLIFICATION METHODS FOR EXTREMELY LOW INPUT NUCLEIC ACIDS

CROSS REFERENCE TO RELATED APPLICATIONS

This application is the U.S. National Stage of International Application No. PCT/US2019/016383, filed Feb. 1, 2019, which was published in English under PCT Article 21(2), which claims the benefit of U.S. Provisional Application No. 62/625,675, filed Feb. 2, 2018. The above-listed applications are herein incorporated by reference in their entirety.

FIELD

This disclosure concerns rapid, one-step or two-step methods for random amplification of very low quantities of DNA and/or RNA present in biological samples.

BACKGROUND

In the majority of biological samples, microbial nucleic acid molecules are present only in minute amounts, which prevents direct sequencing using next-generation sequencing (NGS) platforms such as Illumina (MISEQ™, HISEQ™, NEXTSEQ™ and NOVASEQ™), ION TORRENT™ and NANOPORE™ Currently, 0.1 ng to 10 μg of DNA or cDNA is required for library preparation on most platforms. However, viral or other microbial nucleic acid molecules in clinically relevant biological samples, such as blood, serum, respiratory secretions, cerebral spinal fluid and stool, frequently amounts to less than 0.001 ng. Thus, a need exists for a rapid amplification method capable of amplifying extremely low levels of nucleic acid molecules present in biological samples.

SUMMARY

Methods for the rapid amplification of extremely low quantity nucleic acids in a sample are provided. The disclosed methods are capable of amplifying less than 1 pg of DNA and/or RNA from a biological sample using either one-step or two-step sample preparation.

Provided herein is a method for random amplification of low input nucleic acid (RNA, DNA or a combination thereof). In some embodiments, the method includes mixing in a single container (such as a PCR tube or well of a multiwell plate) a biological sample containing input nucleic acid, a reverse transcriptase, a thermostable DNA polymerase lacking 5' to 3' proofreading exonuclease activity, a hot-start PCR polymerase, a first oligonucleotide, a second oligonucleotide, deoxynucleotide triphosphates (dNTPs) and reaction buffer, wherein the first oligonucleotide is 15 to 30 nucleotides in length and the second oligonucleotide consists of the first oligonucleotide with an additional random nucleotide sequence (polyN) of about 6 to about 10 nucleotides at a 3'-end of the first oligonucleotide; and subjecting the mixture to the following thermocycling steps: an annealing step to permit annealing of the second oligonucleotide to the input nucleic acid, a first synthesis step to permit the reverse transcriptase to generate first strand cDNA, a denaturation step to denature the first strand cDNA from the input nucleic acid and inactivate the reverse transcriptase, a cooling step to permit annealing of the second oligonucleotide to the first strand cDNA, a second synthesis step to permit the thermostable DNA polymerase to generate second strand cDNA, a hot-start PCR polymerase activation step, and PCR using the first oligonucleotide as primer and the second strand cDNA as template.

Also provided is a method for random amplification of low input DNA. In some embodiments, the method includes mixing in a single container (such as a PCR tube or well of a multiwell plate) a biological sample containing input DNA, a thermostable DNA polymerase lacking 5' to 3' proofreading exonuclease activity, a hot-start PCR polymerase, a first oligonucleotide, a second oligonucleotide, dNTPs and reaction buffer, wherein the first oligonucleotide is 15 to 30 nucleotides in length and the second oligonucleotide consists of the first oligonucleotide with an additional polyN sequence of about 6 to about 10 nucleotides at a 3' end of the first oligonucleotide; and subjecting the mixture to the following thermocycling steps: an annealing step to permit annealing of the second oligonucleotide to the input DNA, a first synthesis step to permit the thermostable DNA polymerase to generate first strand cDNA, a denaturation step to denature the first strand cDNA from the input DNA, a cooling step to permit annealing of the second oligonucleotide to the first strand cDNA, a second synthesis step to permit the thermostable DNA polymerase to generate second strand cDNA, a hot-start PCR polymerase activation step, and PCR using the first oligonucleotide as primer and the second strand cDNA as template.

Further provided is a method for random amplification of low input nucleic acid (RNA, DNA or a combination thereof). In some embodiments, the method includes providing a first oligonucleotide and a second oligonucleotide, wherein the first oligonucleotide is 15 to 30 nucleotides in length and the second oligonucleotide consists of the first oligonucleotide with an additional polyN sequence of about 6 to about 10 nucleotides at a 3'-end of the first oligonucleotide; mixing in a first container (such as a PCR tube or well of a multiwell plate) a biological sample containing input nucleic acid, a reverse transcriptase, a thermostable DNA polymerase lacking 5' to 3' proofreading exonuclease activity, the second oligonucleotide, dNTPs and reaction buffer, thereby generating a first mixture; subjecting the first mixture to the following thermocycling steps: an annealing step to permit annealing of the second oligonucleotide to the input nucleic acid, a first synthesis step to permit the reverse transcriptase to generate first strand cDNA, a denaturation step to denature the first strand cDNA from the input nucleic acid and to inactivate the reverse transcriptase, a cooling step to permit annealing of the second oligonucleotide to the first strand cDNA, and a second synthesis step to permit the thermostable DNA polymerase to generate second strand cDNA, thereby producing a second strand cDNA product; mixing in a second container (such as a second PCR tube or second well of a multiwell plate) the second strand cDNA product, a PCR polymerase, the first oligonucleotide, dNTPs and reaction buffer, thereby generating a second mixture; and subjecting the second mixture to the following thermocycling steps: a PCR polymerase activation step, and a PCR using the first oligonucleotide as primer and the second strand cDNA as template.

Also provided are kits for random amplification of low input nucleic acid. In some embodiments, the kit includes a first oligonucleotide and a second oligonucleotide, wherein the first oligonucleotide is 15 to 30 nucleotides in length and the second oligonucleotide consists of the first oligonucleotide with an additional random nucleotide sequence (polyN) of about 6 to about 10 nucleotides at a 3'-end of the first oligonucleotide. In some examples, the kit further includes a reverse transcriptase, a thermostable DNA polymerase lacking 5' to 3' proofreading exonuclease activity, a PCR polymerase (such as a hot-start PCT polymerase), dNTPs, at least one container for performing the amplification (such as PCR tube(s) or multiwell plate(s)), and/or reaction buffer.

The foregoing and other objects and features of the disclosure will become more apparent from the following detailed description, which proceeds with reference to the accompanying figures.

SEQUENCE LISTING

Figure 1:
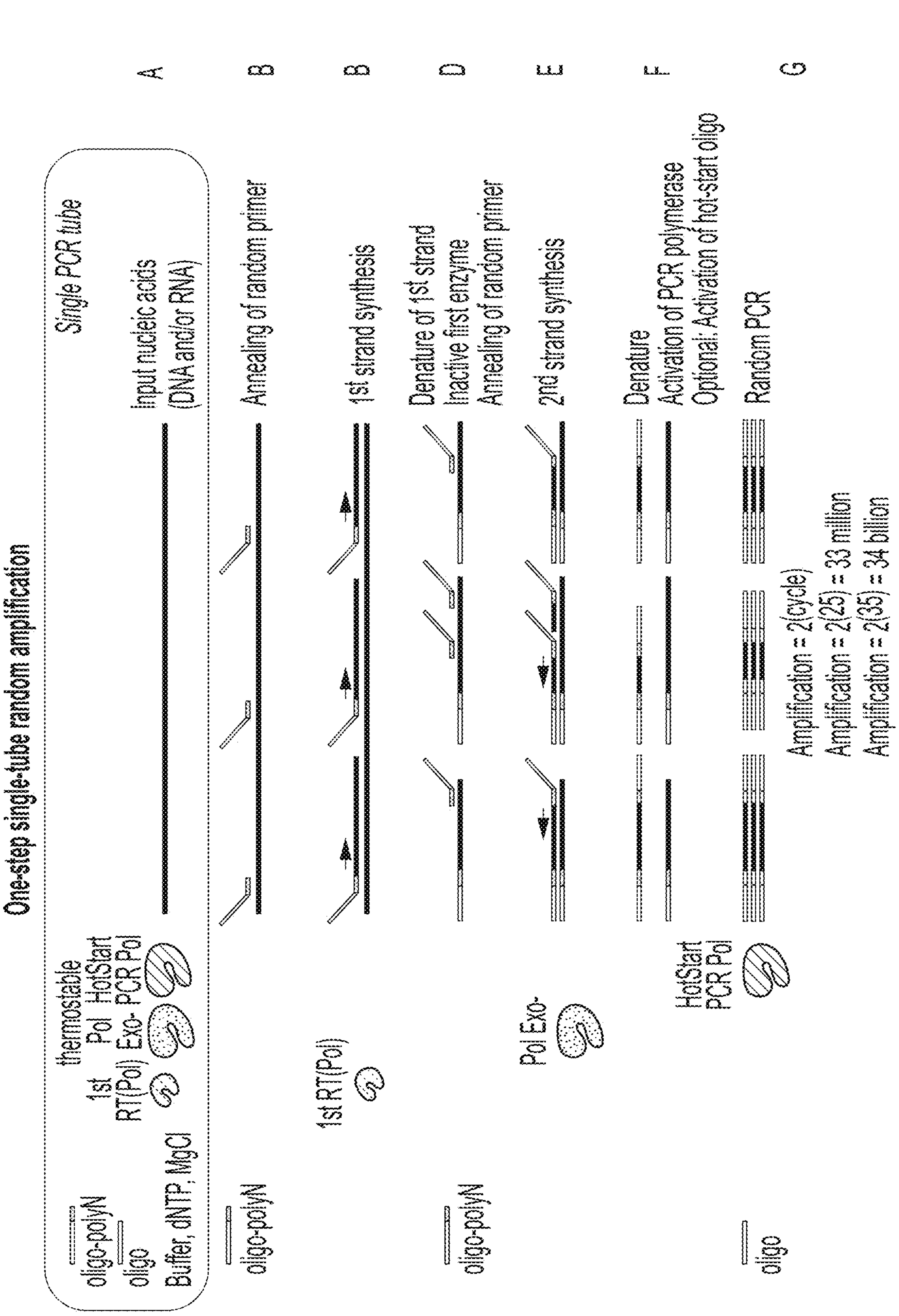
FIG. 1 is a schematic of a one-step, single tube, random nucleic acid amplification method using DNA and/or RNA as the input. Oligo, a primer such as CCTTGAAGGCGGACTGTGAG (SEQ ID NO: 1); Oligo-polyN, a primer with random mixed bases at the 3' end such as CCTTGAAGGCGGACTGTGAGNNNNNNNN (SEQ ID NO: 2); dNTP, deoxynucleotide; MgCl, magnesium chloride; $1^{st}$ RT (Pol), a reverse transcriptase for $1^{st}$ strand complementary DNA (cDNA) synthesis that also has DNA polymerase activity to allow use of DNA as the template; Pol Exo-, a thermostable DNA polymerase that lacks 5' to 3' proofreading exonuclease activity for $2^{nd}$ strand synthesis; HotStart PCR pol, a hot-start PCR polymerase that is only activated in the third stage to perform random PCR amplification.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 28, 2020, 4.09 KB, which is incorporated by reference herein. In the accompanying sequence listing:

SEQ ID NOs: 1-16 are exemplary oligonucleotide primer pairs for use in the disclosed methods.

DETAILED DESCRIPTION

I. Abbreviations cDNA complementary DNA
dNTP deoxynucleotide triphosphate
NGS next-generation sequencing
PCR polymerase chain reaction
Pol polymerase
RT reverse transcriptase

II. Terms and Methods

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Amplification: Increasing the number of copies of a nucleic acid molecule, such as a gene or fragment of a gene. The products of an amplification reaction are called amplification products or amplicons. An example of in vitro amplification is the polymerase chain reaction (PCR), in which a sample (such as a biological sample from a subject) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. "Random amplification" refers to amplification of nucleic acid without regard to the sequence of the nucleic acid (i.e., it does not require sequence-specific primers). Random amplification reactions allow for amplification of total nucleic acid in a sample. Other examples of in vitro amplification techniques include real-time PCR, quantitative real-time PCR (qPCR), reverse transcription PCR (RT-PCR), quantitative RT-PCR (qRT-PCR), loop-mediated isothermal amplification (LAMP; see Notomi et al., *Nucl. Acids Res.* 28:e63, 2000); reverse-transcription LAMP (RT-LAMP); strand displacement amplification (see U.S. Pat. No. 5,744,311); transcription-mediated amplification (U.S. Pat. No. 5,399,491) transcription-free isothermal amplification (see U.S. Pat. No. 6,033,881); repair chain reaction amplification (see WO 90/01069); ligase chain reaction amplification (see U.S. Pat. No. 5,686,272); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, pigs, and cows.

Biological sample: A sample obtained from a subject (such as a human or veterinary subject). Biological samples, include, for example, fluid, cell and/or tissue samples. In some embodiments herein, the biological sample is a fluid sample. Fluid sample include, but are not limited to, serum, urine, blood, plasma, feces, saliva, sputum, cerebral spinal fluid (CSF), fine needle aspirate, and bronchoalveolar lavage (BAL) fluid. Biological samples can also refer to cells or tissue samples, such as biopsy samples, tissue sections, corneal tissue samples, or isolated leukocytes.

Contacting: Placement in direct physical association; includes both in solid and liquid form. "Contacting" is often used interchangeably with "exposed." For example, contacting can occur in vitro with one or more oligonucleotide primers and a biological sample (such as a sample including nucleic acids) in solution.

Control: A reference standard, for example a positive control or negative control. A positive control is known to provide a positive test result. A negative control is known to provide a negative test result. However, the reference standard can be a theoretical or computed result, for example a result obtained in a population.

Hot-start PCR: A modification of PCR that reduces non-specific amplification by inactivation of the DNA polymerase at lower temperatures. In hot-start PCR assays, specific antibodies, aptamers or reversible chemical modifications of the polymerase block the activity of the DNA polymerase at lower temperatures. The DNA polymerase is activated by heating the reaction (such as heating to 95° C.). A "hot-start PCR polymerase" is a DNA polymerase that is modified to prevent activity at lower temperatures. As one non-limiting example, the hot-start DNA polymerase can be modified by addition of heat-labile blocking groups to its amino acid residues. Hot-start DNA polymerases are commercially available, such as from New England Biolabs, Inc. (LongAmp® Hot Start Taq DNA Polymerase, OneTaq® Hot Start DNA Polymerase, Q5® Hot Start DNA Polymerase), Thermo Fisher Scientific (DreamTaq Hot Start DNA Polymerase, Phire Hot Start II DNA Polymerase, Phusion® Hot Start DNA Polymerase, and Maxima Hot Start Taq DNA Polymerase), Sigma-Aldrich (JumpStart Taq DNA Polymerase, and KOD Hot Start DNA Polymerase) and Promega (GoTaq® Hot Start Polymerase), Clontech (Hot Start Takara Taq DNA Polymerase), and QIAGEN (HotStarTaq DNA Polymerase).

Isolated: An "isolated" or "purified" biological component (such as a nucleic acid) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. In some examples, a preparation is purified such that the biological component represents at least 50%, such as at least 70%, at least 90%, at least 95%, or greater, of the total biological component content of the preparation.

Low input nucleic acid: Refers to a very small quantity of nucleic acid. In the context of the present disclosure, a sample with "low input nucleic acid" contains less than 100 ng of nucleic acid (DNA and/or RNA). In some embodiments, the sample contains less than 10 ng, less than 5 ng, less than 1 ng, less than 100 pg, less than 10 pg or less than 1 pg of nucleic acid. In some embodiments, the sample contains 0.005 pg to 100 ng nucleic acid (DNA and/or RNA), 0.005 pg to 50 ng, 0.005 pg to 10 ng, 0.005 pg to 5 ng, 0.005 pg to 1 ng, 0.005 pg to 0.1 pg, 0.01 pg to 100 ng, 0.01 pg to 50 ng, 0.01 pg to 10 ng, 0.01 pg to 5 ng, 0.01 pg to 1 ng, 0.1 pg to 100 ng, 0.1 pg to 50 ng, 0.1 pg to 10 ng, 0.1 pg to 5 ng, 0.1 pg to 1 ng, 1 pg to 100 pg, 1 pg to 10 pg, or 0.5 pg to 1 pg nucleic acid (DNA and/or RNA). In a specific example, a low input nucleic acid is a biological sample containing about 0.005 pg to about 10 ng of input nucleic acid, In a specific example, a low input nucleic acid is a biological sample containing about 0.001 pg to about 10 ng of input nucleic acid, Next generation sequencing (NGS): A nucleic acid sequencing technology which performs sequencing of millions of small nucleic acid fragments (e.g., DNA) in parallel. Bioinformatics analyses are used to piece together these fragments by mapping the individual reads to the reference genome. NGS is unselective, and thus allows for analysis of a genome without bias. In each nucleic acid fragment, the composition and order of the nucleotides are determined by chemical and/or physical methods. Millions of nucleic acid fragments are sequenced in a massively parallel fashion. Examples of such methods include, but are not limited to: those available from Illumina (e.g., sequencing by synthesis (SBS)), ION TORRENT™ (e.g., Ion semiconductor sequencing from ThermoFisher Scientific), Solexa® sequencing, chain termination sequencing (Sanger), or 454 pyrosequencing. NGS is also known as massively parallel or deep sequencing.

Primer: Primers are short nucleic acids, generally DNA oligonucleotides 10 nucleotides or more in length (such as 10-60, 18-22, 15-30, 15-50, 20-40, 20-50, 25-50, or 30-60 nucleotides in length). Primers may be annealed to a complementary target DNA strand by nucleic acid hybridization to form a hybrid between the primer and the target DNA strand, and then extended along the target DNA strand by a DNA polymerase enzyme. Primer pairs or sets of primers (such as 2, 3, 4, 5, 6, or more primers) can be used for amplification of a target nucleic acid, e.g., by PCR, LAMP, RT-LAMP, or other nucleic acid amplification methods known in the art.

Reverse transcriptase (RT): An enzyme that generates complementary DNA from a RNA template. Reverse transcriptases are primarily associated with retroviruses, but this enzyme is also used by other viruses, such as hepatitis B virus. Retroviral RT possesses three different functional activities: RNA-dependent DNA polymerase activity, ribonuclease H activity and DNA-dependent DNA polymerase activity. Reverse transcriptases are commonly used in molecular assays, such as RT-PCR. Exemplary RTs include, but are not limited to, HIV-1 RT, avian myeloblastosis virus (AMV) RT, Moloney murine leukemia virus (MMLV) RT, and recombinant or modified versions thereof.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981*; Needleman & Wunsch, J. Mol. Biol.* 48:443, 1970; Pearson & Lipman, *Proc. Natl. Acad. Sci. USA* 85:2444, 1988*; Higgins & Sharp, Gene,* 73:237-44, 1988*; Higgins & Sharp, CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, MD 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Subject: Living multi-cellular vertebrate organisms, a category that includes both human and non-human animals, such as non-human mammals (such as mice, rats, rabbits, sheep, horses, cows, pigs, and non-human primates). In one example, the subject is a bird, such as a chicken or turkey.

Thermocycling: A series of steps that involves raising and lowering of temperatures for the purpose of amplifying nucleic acid. A basic thermocycling procedure for a standard PCR includes a denaturation step at high temperature (such as 94° C. to 98° C.), an annealing step at a lower temperature that is below the melting temperature of the selected primer(s) (such as 52° C. to 58° C.) and an extension step at a temperature suitable for the DNA polymerase (such as 68° C. to 72° C.). In the context of the present disclosure, thermocycling is used to randomly amplify low input DNA and/or RNA in a sample using a series of steps, such as those shown in FIGS. 1-3 and 5.

Thermolabile: Unstable and/or subject to loss of structural or functional properties at high temperatures.

Thermostable DNA polymerase: A DNA polymerase that retains function at moderate to high temperatures. The DNA-dependent DNA polymerase from *Thermus aquaticus* (Taq) is one example of a thermostable DNA polymerase (for a review, see Ishino and Ishino, *Front Microbiol* 5:465, 2014). Other examples include DNA polymerase from *Thermococcus kodakarensis* (KOD Pol), *Thermococcus litoralis* (Vent Pol), *Thermus* thermophiles (Tth Pol), *Pyrococcus furiosus* (Pfu Pol). An exonuclease minus (Exo-) thermostable DNA polymerase is a thermostable DNA polymerase that lacks both the 5'-3' and 3'-5' exonuclease activities.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

In the majority of clinical specimens, microbial nucleic acid is present in extremely low quantities, presenting a significant challenge to the detection of viral and bacterial pathogens. Similar difficulties exist with detection of low level transcripts, such as cancer-specific transcripts. Although a number of low input nucleic acid amplification methods have been developed, these methods have a limit of detection of 10 ng or greater input target nucleic acid. In addition, previous random amplification methods involve many procedures that require manual or automated addition of components, through steps or stages of the workflow. To enable rapid detection of minute quantities of nucleic acid (such as microbial nucleic acid) in biological samples, the present disclosure describes a one-step, single-tube method for random amplification of nucleic acid that is capable of detecting as little as 0.005 pg input target nucleic acid, which is about 10,000 times more sensitive than currently available commercial kits and methods. The present disclosure further describes a two-step method for random amplification of low input nucleic acid with similar sensitivity. Using the disclosed methods, amplicons are produced in amounts sufficient for next-generation sequencing (NGS) or other sequencing platforms. As compared to polymerase chain reaction (PCR), which amplifies a single target, random amplification allows nonbiased universal amplification of all nucleic acid in a sample. Random amplification eliminates the need for microorganism-specific primer design and allows amplification of unknown microorganisms without prior sequence knowledge.

A. One-Step Method for Random Amplification of RNA and/or DNA

Provided herein are methods for the random amplification of low input nucleic acid (for example, target nucleic acid molecule), wherein the input nucleic acid is DNA, RNA or a combination thereof. In some embodiments, the method includes mixing in a single container a biological sample containing input nucleic acid, a reverse transcriptase, a thermostable DNA polymerase lacking 5' to 3' proofreading exonuclease activity, a hot-start PCR polymerase, a first oligonucleotide, a second oligonucleotide, deoxynucleotide triphosphates (dNTPs) and reaction buffer; and subjecting the mixture to a series of thermocycling steps. In some examples, the mixture also includes MgCl, dithiothreitol (DTT) and/or RNase inhibitor. In some examples, the single container is a container, tube, or vial made of plastic or other suitable material, such as a PCR tube or well of a multi-well plate (such as a 96- or 384-well plate).

In some embodiments, the first oligonucleotide is 15 to 30 nucleotides in length (such as 15 to 25, 15 to 20, or 15 to 18 nucleotides) and the second oligonucleotide consists of the first oligonucleotide with an additional polyN sequence of about 6 to about 10 nucleotides (such as 6, 7, 8, 9 or 10 nucleotides) at a 3' end of the first oligonucleotide.

In some embodiments, the thermocycling steps include an annealing step to permit annealing (e.g., hybridization) of the second oligonucleotide to the input nucleic acid; a first synthesis step to permit the reverse transcriptase to generate first strand cDNA; a denaturation step to denature the first strand cDNA from the input nucleic acid and inactivate the reverse transcriptase; a cooling step to permit annealing of the second oligonucleotide to the first strand cDNA; a second synthesis step to permit the thermostable DNA polymerase to generate second strand cDNA; a hot-start PCR polymerase activation step; and PCR using the first oligonucleotide as primer and the second strand cDNA as template.

In some embodiments, the input nucleic acid comprises or consists of RNA (such as mRNA or miRNA). In other embodiments, the input nucleic acid comprises or consists of DNA (such as genomic DNA or cDNA). In yet other examples, the input nucleic acid comprises a combination or mixture of RNA and DNA.

In some embodiments, the input nucleic acid comprises viral nucleic acid molecules. In some embodiments, the input nucleic acid comprises bacterial nucleic acid molecules. In some embodiments, the input nucleic acid comprises a combination of viral and bacterial nucleic acid molecules. Specific examples are provided herein.

In some embodiments, the biological sample contains less than 10 ng of input nucleic acid, such as less than 5 ng, less than 1 ng, less than 100 pg, less than 10 pg, less than 1 pg, less than 0.5 pg, less than 0.1 pg, less than 0.05 pg, less than 0.01 pg, or less than 0.005 pg input nucleic acid. In some examples, the biological sample contains about 0.001 pg to about 10 ng of input nucleic acid, such as about 0.002 pg to about 5 ng, about 0.003 to about 1 ng, about 0.004 to about 100 pg or about 0.005 pg to about 10 pg. In a specific example, the biological sample contains about 0.005 pg to about 10 ng of input nucleic acid, In a specific example, the biological sample contains about 0.001 pg to about 10 ng of input nucleic acid, In some embodiments, the annealing step is performed at about 23° C. to about 52° C., such as about 25° C., about 30° C., about 35° C., about 40° C., about 45° C. or about 50° C.

In some embodiments, the first synthesis step is performed at about 40° C. to about 60° C., such as about 40° C., about 45° C., about 50° C., about 55° C. or about 60° C.

In some embodiments, the denaturation step is performed at about 92° C. to about 98° C., such as about 92° C., about 93° C., about 94° C., about 95° C., about 96° C., about 97° C. or about 98° C.

In some embodiments, the cooling step is performed at or below 55° C., such as about 4° C. to about 55° C., such as about 4° C., about 10° C. about 15° C., about 20°, about 25°, about 30° C., about 35° C., about 40° C., about 45° C. or about 55° C.

In some embodiments, the second synthesis step is performed at about 60° C. to about 72° C., such as about 60° C., about 61° C., about 62° C., about 63° C., about 64° C., about 65° C., about 66° C., about 67° C., about 68° C., about 69° C., about 70° C., about 71° C. or about 72° C.

In some embodiments, the hot-start polymerase activation step is performed at about 92° C. to about 98° C., such as about 92° C., about 93° C., about 94° C., about 95° C., about 96° C., about 97° C. or about 98° C.

In some examples, the first oligonucleotide is about 15 to about 25 nucleotides in length, such as about 18 to about 22 nucleotides in length or about 19 to about 21 nucleotides in length. In some examples, the first oligonucleotide is about 15, about 16, about 17, about 18, about 19 about 20, about 21, about 22, about 23, about 24 or about 25 nucleotides in length. In specific non-limiting examples, the first oligonucleotide is 20 nucleotides in length. In some examples, the first oligonucleotide has a sequence that is not found in the species from which the biological sample was taken. In particular non-limiting examples, the first oligonucleotide comprises or consists of the nucleotide sequence CCTTGAAGGCGGACTGTGAG (SEQ ID NO: 1), CCTTGAAGGCGGACTGTGAG (SEQ ID NO: 3), GTCGGTGTCACTCTACTGCC (SEQ ID NO: 5), CGATCCGACAACACACGCTG (SEQ ID NO: 7), AGTCTCGTCGTAGGCTGCTG (SEQ ID NO: 9), CTACACATAGGCGTCCCGTG (SEQ ID NO: 11), ATCTACGAGCCGTCTGTGTC (SEQ ID NO: 13) or CTACACATCAACACACGCTG (SEQ ID NO: 15).

In some examples, the first oligonucleotide is a hot-start oligo that is activated at higher temperatures, such as during the hot-start PCR polymerase activation step (see FIG. 1, step F). In specific examples, the first oligonucleotide comprises a thermolabile phosphotriester modification at the 3' terminal internucleotide linkage and/or at the 3' penultimate internucleotide linkage.

In some examples, the second oligonucleotide is about 21 to about 35 nucleotides in length, such as about 24 to about 32 nucleotides in length, about 25 to about 31, or about 26 to about 29 nucleotides in length. In some examples, the first oligonucleotide is about 21, about 22, about 23, about 24, about 25 about 26, about 27, about 28, about 29, about 30, about 31, about 32, about 33, about 34 or about 35 nucleotides in length. In specific non-limiting examples, the second oligonucleotide is 28 nucleotides in length. In one example, the second oligonucleotide comprises or consists of the nucleotide sequence CCTTGAAGGCGGACTGTGAGNNNNNNNN (SEQ ID NO: 2), CCTTGAAGGCGGACTGTGAGNNNNNNN (SEQ ID NO: 4), GTCGGTGTCACTCTACTGCCNNNNNNNN (SEQ ID NO: 6), CGATCCGACAACACACGCTGNNNNNNNN (SEQ ID NO: 8), AGTCTCGTCGTAGGCTGCTGNNNNNNNN (SEQ ID NO: 10), CTACACATAGGCGTCCCGTGNNNNNNNN (SEQ ID NO: 12), ATCTACGAGCCGTCTGTGTCNNNNNNNN (SEQ ID NO: 14), or CTACACATCAACACACGCTGNNNNNNNN (SEQ ID NO: 16).

B. One-Step Method for Random Amplification of DNA

Further provided herein are methods for the random amplification of low input nucleic acid, wherein the input nucleic acid is DNA. In some embodiments, the method includes mixing in a single container a biological sample containing input DNA, a thermostable DNA polymerase lacking 5' to 3' proofreading exonuclease activity, a hot-start PCR polymerase, a first oligonucleotide, a second oligonucleotide, dNTPs and reaction buffer; and subjecting the mixture to a series of thermocycling steps. In some examples, the mixture also includes typical reverse transcription components such as MgCl, DTT and/or RNase inhibitor. In some examples, the single container is a container, tube or vial made of plastic or other suitable material, such as a PCR tube or well of a multi-well plate (such as a 96- or 384-well plate).

In some embodiments, the first oligonucleotide is 15 to 30 nucleotides in length and the second oligonucleotide consists of the first oligonucleotide with an additional polyN sequence of about 6 to about 10 nucleotides at a 3' end of the first oligonucleotide.

In some embodiments, the thermocycling steps include an annealing step to permit annealing of the second oligonucleotide to the input DNA; a first synthesis step to permit the thermostable DNA polymerase to generate first strand cDNA; a denaturation step to denature the first strand cDNA from the input DNA; a cooling step to permit annealing of the second oligonucleotide to the first strand cDNA; a second synthesis step to permit the thermostable DNA polymerase to generate second strand cDNA; a hot-start PCR polymerase activation step; and PCR using the first oligonucleotide as primer and the second strand cDNA as template.

In some embodiments, the input DNA comprises or consists of viral DNA molecules. In some embodiments, the input DNA comprises or consists of bacterial DNA molecules. In some embodiments, the input DNA comprises a combination of viral and bacterial DNA molecules.

In some embodiments, the biological sample contains less than 10 ng of input DNA, such as less than 5 ng, less than 1 ng, less than 100 pg, less than 10 pg, less than 1 pg, less than 0.5 pg, less than 0.1 pg, less than 0.05 pg, less than 0.01 pg, or less than 0.005 pg input DNA. In some examples, the biological sample contains about 0.001 pg to about 10 ng of input DNA, such as about 0.002 pg to about 5 ng, about 0.003 to about 1 ng, about 0.004 to about 100 pg or about 0.005 pg to about 10 pg DNA. In a specific example, the biological sample contains about 0.005 pg to about 10 ng of input nucleic acid, In a specific example, the biological sample contains about 0.001 pg to about 10 ng of input nucleic acid, In some embodiments, the annealing step is performed at about 23° C. to about 52° C., such as about 25° C., about 30° C., about 35° C., about 40° C., about 45° C. or about 50° C.

In some embodiments, the first synthesis step is performed at about 40° C. to about 60° C., such as about 40° C., about 45° C., about 50° C., about 55° C. or about 60° C.

In some embodiments, the denaturation step is performed at about 92° C. to about 98° C., such as about 92° C., about 93° C., about 94° C., about 95° C., about 96° C., about 97° C. or about 98° C.

In some embodiments, the cooling step is performed at or below 55° C., such as about 4° C. to about 55° C., such as about 4° C., about 10° C. about 15° C., about 20°, about 25°, about 30° C., about 35° C., about 40° C., about 45° C. or about 55° C.

In some embodiments, the second synthesis step is performed at about 60° C. to about 72° C., such as about 60° C., about 61° C., about 62° C., about 63° C., about 64° C., about 65° C., about 66° C., about 67° C., about 68° C., about 69° C., about 70° C., about 71° C. or about 72° C.

In some embodiments, the hot-start polymerase activation step is performed at about 92° C. to about 98° C., such as about 92° C., about 93° C., about 94° C., about 95° C., about 96° C., about 97° C. or about 98° C.

In some examples, the first oligonucleotide is about 15 to about 25 nucleotides in length, such as about 18 to about 22 nucleotides in length or about 19 to about 21 nucleotides in length. In some examples, the first oligonucleotide is about 15, about 16, about 17, about 18, about 19 about 20, about 21, about 22, about 23, about 24 or about 25 nucleotides in length. In specific non-limiting examples, the first oligonucleotide is 20 nucleotides in length. In some examples, the first oligonucleotide has a sequence that is not found in the species from which the biological sample was taken. In particular non-limiting examples, the first oligonucleotide comprises or consists of the nucleotide sequence CCTTGAAGGCGGACTGTGAG (SEQ ID NO: 1), CCTTGAAGGCGGACTGTGAG (SEQ ID NO: 3), GTCGGTGTCACTCTACTGCC (SEQ ID NO: 5), CGATCCGACAACACACGCTG (SEQ ID NO: 7), AGTCTCGTCGTAGGCTGCTG (SEQ ID NO: 9), CTACACATAGGCGTCCCGTG (SEQ ID NO: 11), ATCTACGAGCCGTCTGTGTC (SEQ ID NO: 13) or CTACACATCAACACACGCTG (SEQ ID NO: 15).

Figure 3:
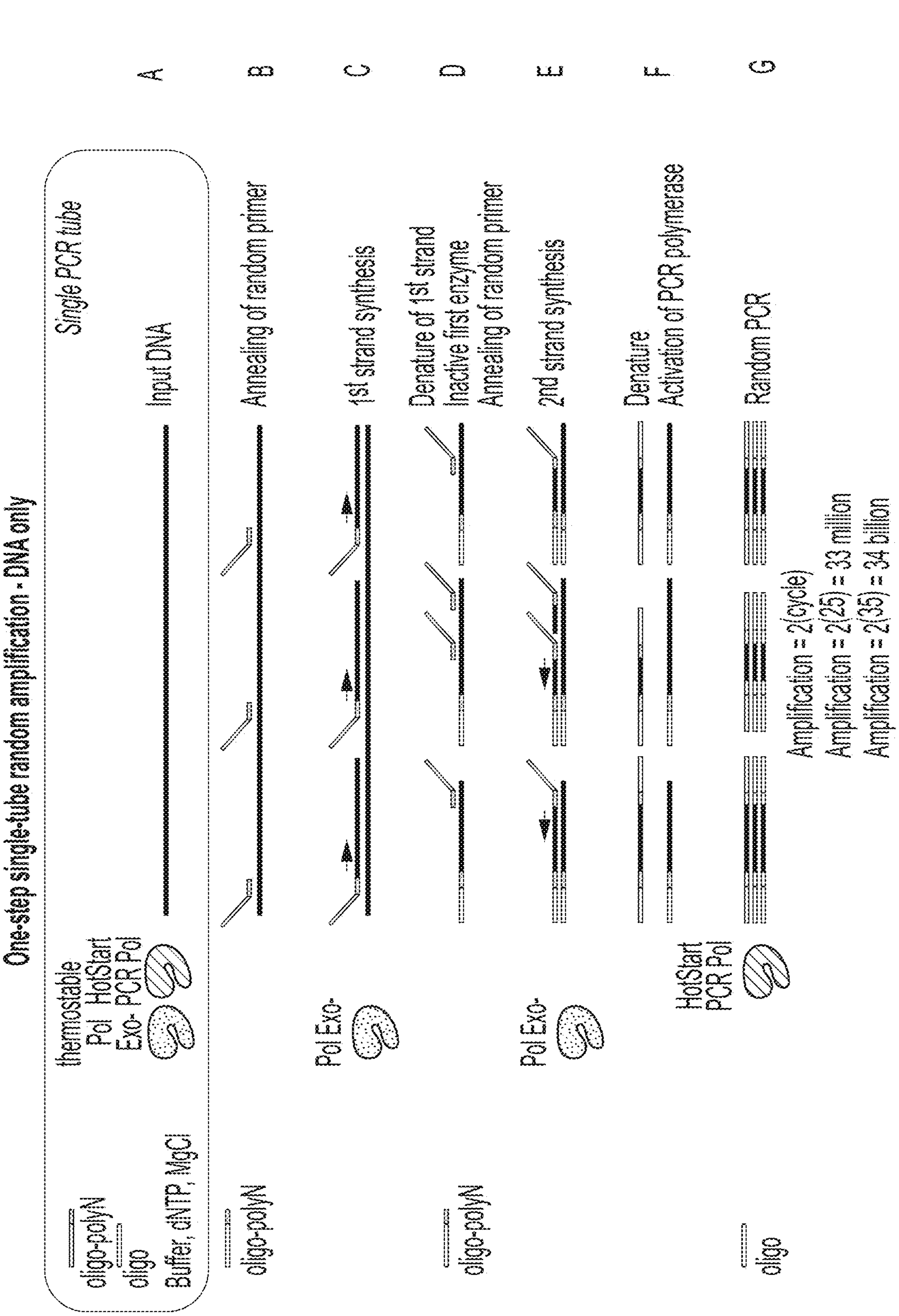
FIG. 3 is a schematic of a one-step, single tube, random nucleic acid amplification method using only DNA as the input. The illustrated method is a modification of the method shown in FIG. 1. Oligo, a primer such as CCTTGAAGGCGGACTGTGAG (SEQ ID NO: 1); Oligo-polyN, a primer with random mixed bases at the 3' end such as CCTTGAAGGCGGACTGTGAGNNNNNNNN (SEQ ID NO: 2); dNTP, deoxynucleotide; MgCl, magnesium chloride; Pol Exo-, a thermostable DNA polymerase that lacks 5' to 3' proofreading exonuclease activity for $2^{nd}$ strand synthesis; HotStart PCR Pol, a hot-start PCR polymerase that is only activated in the third stage to perform random PCR amplification.

In some examples, the first oligonucleotide is a hot-start oligo that is activated at higher temperatures, such as during the hot-start PCR polymerase activation step (see FIG. 3, step F). In specific examples, the first oligonucleotide comprises a thermolabile phosphotriester modification at the 3' terminal internucleotide linkage and/or at the 3' penultimate internucleotide linkage.

In some examples, the second oligonucleotide is about 21 to about 35 nucleotides in length, such as about 24 to about 32 nucleotides in length, about 25 to about 31, or about 26 to about 29 nucleotides in length. In some examples, the first oligonucleotide is about 21, about 22, about 23, about 24, about 25 about 26, about 27, about 28, about 29, about 30, about 31, about 32, about 33, about 34 or about 35 nucleotides in length. In specific non-limiting examples, the second oligonucleotide is 28 nucleotides in length. In one example, the second oligonucleotide comprises or consists of the nucleotide sequence CCTTGAAGGCGGACTGTGAGNNNNNNNN (SEQ ID NO: 2), CCTTGAAGGCGGACTGTGAGNNNNNN (SEQ ID NO: 4), GTCGGTGTCACTCTACTGCCNNNNNNNN (SEQ ID NO: 6), CGATCCGACAACACACGCTGNNNNNNNN (SEQ ID NO: 8), AGTCTCGTCGTAGGCTGCTGNNNNNNNN (SEQ ID NO: 10), CTACACATAGGCGTCCCGTGNNNNNNNN (SEQ ID NO: 12), ATCTACGAGCCGTCTGTGTCNNNNNNNN (SEQ ID NO: 14), or CTACACATCAACACACGCTGNNNNNNNN (SEQ ID NO: 16).

C. Two-Step Method for Random Amplification of RNA and/or DNA

Also provided herein is a two-step method for the random amplification of low input nucleic acid (for example, target nucleic acid molecule), wherein the input nucleic acid is DNA, RNA or a combination thereof. In the two-step method, the first step includes a first container in which $1^{st}$ strand synthesis and $2^{nd}$ strand synthesis are performed, and the second step uses a second container in which the PCR step is performed. In some examples, the first and second containers are containers or vials or tubes made of plastic or other suitable material, such as separate PCR tubes or separate wells of a multi-well plate(s) (such as a 96- or 384-well plate(s)).

In some embodiments, the method includes providing a first oligonucleotide and a second oligonucleotide; mixing in a first container a biological sample containing input nucleic acid, a reverse transcriptase, a thermostable DNA polymerase lacking 5' to 3' proofreading exonuclease activity, the second oligonucleotide, dNTPs and reaction buffer to generate a first mixture; and subjecting the first mixture to a series of thermocycling steps. In some examples, the thermocycling steps for the first mixture include an annealing step to permit annealing (e.g., hybridization) of the second oligonucleotide to the input nucleic acid; a first synthesis step to permit the reverse transcriptase to generate first strand cDNA; a denaturation step to denature the first strand cDNA from the input nucleic acid and inactivate the reverse transcriptase; a cooling step to permit annealing of the second oligonucleotide to the first strand cDNA; and a second synthesis step to permit the thermostable DNA polymerase to generate second strand cDNA. In some embodiments, the method further includes mixing in a second container the second strand cDNA product, a PCR polymerase, the first oligonucleotide, dNTPs and reaction buffer, thereby generating a second mixture; and subjecting the second mixture to a series of thermocycling steps. In some examples, the thermocycling steps for the second mixture include a PCR polymerase activation step (labelled as "Denature" in FIG. 5, step F), and a PCR using the first oligonucleotide as primer and the second strand cDNA as template. Thus, in some examples, the second strand cDNA product is transferred from the first container into the second container (e.g., introduced into the second container), which may include or have subsequently added thereto, a PCR polymerase, the first oligonucleotide, dNTPs and reaction buffer.

In some embodiments, the first and/or second mixture also include MgCl, DTT and/or RNase inhibitor.

In some embodiments, the first oligonucleotide is 15 to 30 nucleotides in length (such as 15 to 25, 15 to 20, or 15 to 18 nucleotides) and the second oligonucleotide consists of the first oligonucleotide with an additional polyN sequence of about 6 to about 10 nucleotides (such as 6, 7, 8, 9 or 10 nucleotides) at a 3' end of the first oligonucleotide.

In some embodiments, the input nucleic acid comprises or consists of RNA (such as mRNA or miRNA). In other embodiments, the input nucleic acid comprises or consists of DNA (such as genomic DNA or cDNA). In yet other examples, the input nucleic acid comprises a combination or mixture of RNA and DNA.

In some embodiments, the input nucleic acid comprises viral nucleic acid molecules. In some embodiments, the input nucleic acid comprises bacterial nucleic acid molecules. In some embodiments, the input nucleic acid comprises a combination of viral and bacterial nucleic acid molecules. Specific examples are provided herein.

In some embodiments, the biological sample contains less than 10 ng of input nucleic acid, such as less than 5 ng, less than 1 ng, less than 100 pg, less than 10 pg, less than 1 pg, less than 0.5 pg, less than 0.1 pg, less than 0.05 pg, less than 0.01 pg, or less than 0.005 pg input nucleic acid. In some examples, the biological sample contains about 0.001 pg to about 10 ng of input nucleic acid, such as about 0.002 pg to about 5 ng, about 0.003 to about 1 ng, about 0.004 to about 100 pg or about 0.005 pg to about 10 pg. In a specific example, the biological sample contains about 0.005 pg to about 10 ng of input nucleic acid, In a specific example, the biological sample contains about 0.001 pg to about 10 ng of input nucleic acid, In some embodiments, the annealing step is performed at about 23° C. to about 52° C., such as about 25° C., about 30° C., about 35° C., about 40° C., about 45° C. or about 50° C.

In some embodiments, the first synthesis step is performed at about 40° C. to about 60° C., such as about 40° C., about 45° C., about 50° C., about 55° C. or about 60° C.

In some embodiments, the denaturation step is performed at about 92° C. to about 98° C., such as about 92° C., about 93° C., about 94° C., about 95° C., about 96° C., about 97° C. or about 98° C.

In some embodiments, the cooling step is performed at or below 55° C., such as about 4° C. to about 55° C., such as about 4° C., about 10° C. about 15° C., about 20°, about 25°, about 30° C., about 35° C., about 40° C., about 45° C. or about 55° C.

In some embodiments, the second synthesis step is performed at about 60° C. to about 72° C., such as about 60° C., about 61° C., about 62° C., about 63° C., about 64° C., about 65° C., about 66° C., about 67° C., about 68° C., about 69° C., about 70° C., about 71° C. or about 72° C.

In some embodiments, the PCR polymerase activation step is performed at about 92° C. to about 98° C., such as about 92° C., about 93° C., about 94° C., about 95° C., about 96° C., about 97° C. or about 98° C.

In some examples, the first oligonucleotide is about 15 to about 25 nucleotides in length, such as about 18 to about 22 nucleotides in length or about 19 to about 21 nucleotides in length. In some examples, the first oligonucleotide is about 15, about 16, about 17, about 18, about 19 about 20, about 21, about 22, about 23, about 24 or about 25 nucleotides in length. In specific non-limiting examples, the first oligonucleotide is 20 nucleotides in length. In some examples, the first oligonucleotide has a sequence that is not found in the species from which the biological sample was taken. In particular non-limiting examples, the first oligonucleotide comprises or consists of the nucleotide sequence CCTT-GAAGGCGGACTGTGAG (SEQ ID NO: 1), CCTT-GAAGGCGGACTGTGAG (SEQ ID NO: 3), GTCGGTGT-CACTCTACTGCC (SEQ ID NO: 5), CGATCCGACAACACACGCTG (SEQ ID NO: 7), AGTCTCGTCGTAGGCTGCTG (SEQ ID NO: 9), CTA-CACATAGGCGTCCCGTG (SEQ ID NO: 11), ATC-TACGAGCCGTCTGTGTC (SEQ ID NO: 13) or CTACA-CATCAACACACGCTG (SEQ ID NO: 15).

Figure 5:
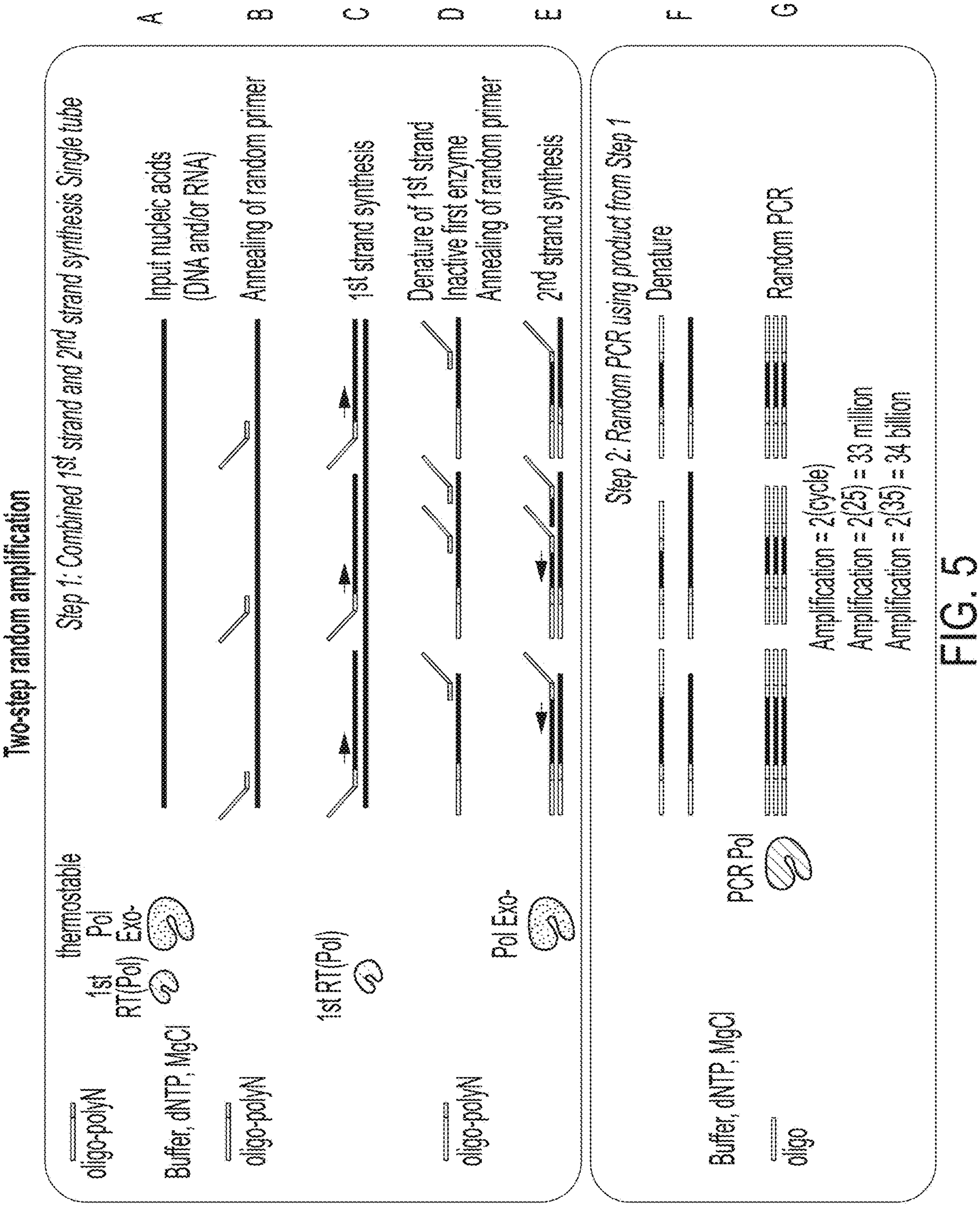
FIG. 5 is a schematic of a two-step random nucleic acid amplification method using DNA and/or RNA as the input. This method is similar to the methods shown in FIGS. 1 and 2, but in the two-step method, $1^{st}$ strand and $2^{nd}$ strand synthesis occur in the first step and the product is transferred to a second tube to perform the random PCR step.

In some examples, the first oligonucleotide is a hot-start oligo that is activated at higher temperatures, such as during the PCR polymerase activation step (see FIG. 5, step F, labelled as "Denature"). In specific examples, the first oligonucleotide comprises a thermolabile phosphotriester modification at the 3'-terminal internucleotide linkage and/or at the 3'-penultimate internucleotide linkage.

In some examples, the second oligonucleotide is about 21 to about 35 nucleotides in length, such as about 24 to about 32 nucleotides in length, about 25 to about 31, or about 26 to about 29 nucleotides in length. In some examples, the first oligonucleotide is about 21, about 22, about 23, about 24, about 25 about 26, about 27, about 28, about 29, about 30, about 31, about 32, about 33, about 34 or about 35 nucleotides in length. In specific non-limiting examples, the second oligonucleotide is 28 nucleotides in length. In one example, the second oligonucleotide comprises or consists of the nucleotide sequence CCTTGAAGGCGGACTGTGAG-NNNNNNNN (SEQ ID NO: 2), CCTT-GAAGGCGGACTGTGAGNNNNNN (SEQ ID NO: 4), GTCGGTGTCACTCTACTGCCNNNNNNNN (SEQ ID NO: 6), CGATCCGACAACACACGCTGNNNNNNNN (SEQ ID NO: 8), AGTCTCGTCGTAGGCTGCTGNNNNNNNN (SEQ ID NO: 10), CTACACATAGGCGTCCCGTGNNNNNNNN (SEQ ID NO: 12), ATC-TACGAGCCGTCTGTGTCNNNNNNNN (SEQ ID NO: 14), or CTACACATCAACACACGCTGNNNNNNNN (SEQ ID NO: 16).

D. Two-Step Method for Random Amplification of DNA

Further provided herein is a two-step method for the random amplification of low input nucleic acid (for example, target nucleic acid molecule), wherein the input nucleic acid is DNA. In the two-step method, the first step includes a first container in which Pt strand synthesis and $2^{nd}$ strand synthesis are performed, and the second step uses a second container in which random PCR is performed. In some examples, the first and second containers are containers or vials or tubes made of plastic or other suitable material, such as separate PCR tubes or separate wells of a multi-well plate(s) (such as a 96- or 384-well plate(s)).

In some embodiments, the method includes providing a first oligonucleotide and a second oligonucleotide; mixing in a first container a biological sample containing input DNA, a thermostable DNA polymerase lacking 5' to 3' proofreading exonuclease activity, the second oligonucleotide, dNTPs and reaction buffer to generate a first mixture; and subjecting the first mixture to a series of thermocycling steps. In some examples, the thermocycling steps include an annealing step to permit annealing of the second oligonucleotide to the input DNA; a first synthesis step to permit the thermostable DNA polymerase to generate first strand cDNA; a denaturation step to denature the first strand cDNA from the input DNA; a cooling step to permit annealing of the second oligonucleotide to the first strand cDNA; and a second synthesis step to permit the thermostable DNA polymerase to generate second strand cDNA. In some embodiments, the method further includes mixing in a second container the second strand cDNA product, a PCR polymerase, the first oligonucleotide, dNTPs and reaction buffer, thereby generating a second mixture; and subjecting the second mixture to a series of thermocycling steps. In some examples, the thermocycling steps for the second mixture include a PCR polymerase activation step (labelled as “Denature” in FIG. 6, step F), and a random PCR using the first oligonucleotide as primer and the second strand cDNA as template. Thus, in some examples, the second strand cDNA product is transferred from the first container into the second container (e.g., introduced into the second container), which may include or have subsequently added thereto, a PCR polymerase, the first oligonucleotide, dNTPs and reaction buffer.

In some embodiments, the first and/or second mixture also include MgCl, DTT and/or RNase inhibitor.

In some embodiments, the first oligonucleotide is 15 to 30 nucleotides in length (such as 15 to 25, 15 to 20, or 15 to 18 nucleotides) and the second oligonucleotide consists of the first oligonucleotide with an additional polyN sequence of about 6 to about 10 nucleotides (such as 6, 7, 8, 9 or 10 nucleotides) at a 3' end of the first oligonucleotide.

In some embodiments, the input nucleic acid comprises or consists of RNA (such as mRNA or miRNA). In other embodiments, the input nucleic acid comprises or consists of DNA (such as genomic DNA or cDNA). In yet other examples, the input nucleic acid comprises a combination or mixture of RNA and DNA.

In some embodiments, the input nucleic acid comprises viral nucleic acid molecules. In some embodiments, the input nucleic acid comprises bacterial nucleic acid molecules. In some embodiments, the input nucleic acid comprises a combination of viral and bacterial nucleic acid molecules. Specific examples are provided herein.

In some embodiments, the biological sample contains less than 10 ng of input nucleic acid, such as less than 5 ng, less than 1 ng, less than 100 pg, less than 10 pg, less than 1 pg, less than 0.5 pg, less than 0.1 pg, less than 0.05 pg, less than 0.01 pg, or less than 0.005 pg input nucleic acid. In some examples, the biological sample contains about 0.001 pg to about 10 ng of input nucleic acid, such as about 0.002 pg to about 5 ng, about 0.003 to about 1 ng, about 0.004 to about 100 pg or about 0.005 pg to about 10 pg. In a specific example, the biological sample contains about 0.005 pg to about 10 ng of input nucleic acid, In a specific example, the biological sample contains about 0.001 pg to about 10 ng of input nucleic acid, In some embodiments, the annealing step is performed at about 23° C. to about 52° C., such as about 25° C., about 30° C., about 35° C., about 40° C., about 45° C. or about 50° C.

In some embodiments, the first synthesis step is performed at about 40° C. to about 60° C., such as about 40° C., about 45° C., about 50° C., about 55° C. or about 60° C.

In some embodiments, the denaturation step is performed at about 92° C. to about 98° C., such as about 92° C., about 93° C., about 94° C., about 95° C., about 96° C., about 97° C. or about 98° C.

In some embodiments, the cooling step is performed at or below 55° C., such as about 4° C. to about 55° C., such as about 4° C., about 10° C. about 15° C., about 20°, about 25°, about 30° C., about 35° C., about 40° C., about 45° C. or about 55° C.

In some embodiments, the second synthesis step is performed at about 60° C. to about 72° C., such as about 60° C., about 61° C., about 62° C., about 63° C., about 64° C., about 65° C., about 66° C., about 67° C., about 68° C., about 69° C., about 70° C., about 71° C. or about 72° C.

In some embodiments, the PCR polymerase activation step is performed at about 92° C. to about 98° C., such as about 92° C., about 93° C., about 94° C., about 95° C., about 96° C., about 97° C. or about 98° C.

In some examples, the first oligonucleotide is about 15 to about 25 nucleotides in length, such as about 18 to about 22 nucleotides in length or about 19 to about 21 nucleotides in length. In some examples, the first oligonucleotide is about 15, about 16, about 17, about 18, about 19 about 20, about 21, about 22, about 23, about 24 or about 25 nucleotides in length. In specific non-limiting examples, the first oligonucleotide is 20 nucleotides in length. In some examples, the first oligonucleotide has a sequence that is not found in the species from which the biological sample was taken. In particular non-limiting examples, the first oligonucleotide comprises or consists of the nucleotide sequence CCTT-GAAGGCGGACTGTGAG (SEQ ID NO: 1), CCTT-GAAGGCGGACTGTGAG (SEQ ID NO: 3), GTCGGTGT-CACTCTACTGCC (SEQ ID NO: 5), CGATCCGACAACACACGCTG (SEQ ID NO: 7), AGTCTCGTCGTAGGCTGCTG (SEQ ID NO: 9), CTA-CACATAGGCGTCCCGTG (SEQ ID NO: 11), ATC-TACGAGCCGTCTGTGTC (SEQ ID NO: 13) or CTACA-CATCAACACACGCTG (SEQ ID NO: 15).

Figure 6:
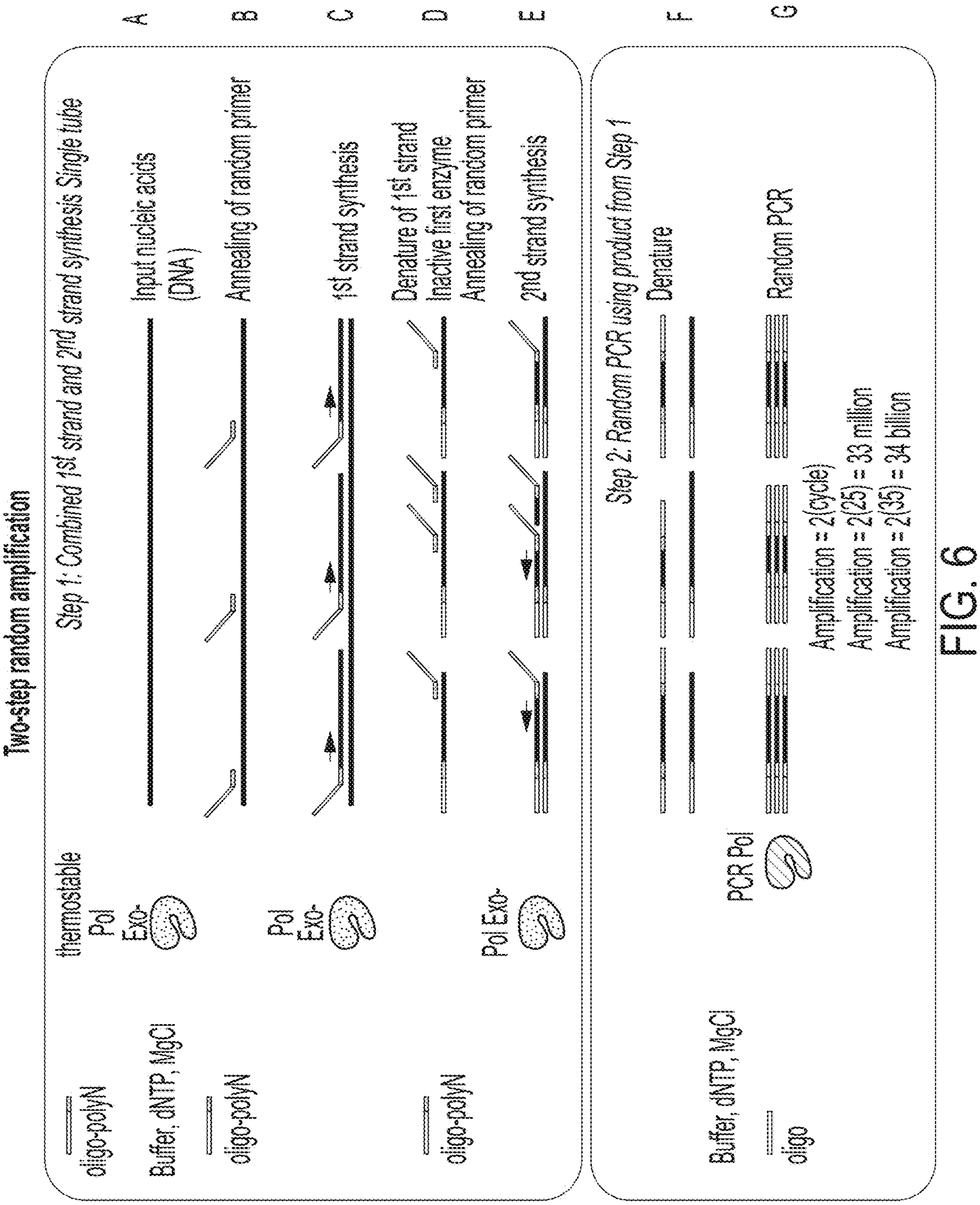
FIG. 6 is a schematic of a two-step random nucleic acid amplification method using only DNA as the input. This method is similar to the method shown in FIG. 3, but in the two-step method, $1^{st}$ strand and $2^{nd}$ strand synthesis occur in the first step and the product is transferred to a second tube to perform the random PCR step.

In some examples, the first oligonucleotide is a hot-start oligo that is activated at higher temperatures, such as during the PCR polymerase activation step (see FIG. 6, step F, labelled as "Denature"). In specific examples, the first oligonucleotide comprises a thermolabile phosphotriester modification at the 3'-terminal internucleotide linkage and/or at the 3'-penultimate internucleotide linkage.

In some examples, the second oligonucleotide is about 21 to about 35 nucleotides in length, such as about 24 to about 32 nucleotides in length, about 25 to about 31, or about 26 to about 29 nucleotides in length. In some examples, the first oligonucleotide is about 21, about 22, about 23, about 24, about 25 about 26, about 27, about 28, about 29, about 30, about 31, about 32, about 33, about 34 or about 35 nucleotides in length. In specific non-limiting examples, the second oligonucleotide is 28 nucleotides in length. In one example, the second oligonucleotide comprises or consists of the nucleotide sequence CCTTGAAGGCGGACTGTGAG-NNNNNNNN (SEQ ID NO: 2), CCTTGAAGGCGGACTGTGAGNNNNNN (SEQ ID NO: 4), GTCGGTGTCACTCTACTGCCNNNNNNNN (SEQ ID NO: 6), CGATCCGACAACACACGCTGNNNNNNNN (SEQ ID NO: 8), AGTCTCGTCGTAGGCTGCTGNNNNNNNN (SEQ ID NO: 10), CTACACATAGGCGTCCCGTGNNNNNNNN (SEQ ID NO: 12), ATCTACGAGCCGTCTGTGTCNNNNNNNN (SEQ ID NO: 14), or CTACACATCAACACACGCTGNNNNNNN (SEQ ID NO: 16).

E. Kits for Random Amplification of Nucleic Acid

Kits for random amplification of low input nucleic acid are also described. In some embodiments, the kit includes a first oligonucleotide and a second oligonucleotide, wherein the first oligonucleotide is 15 to 30 nucleotides in length and the second oligonucleotide consists of the first oligonucleotide with an additional polyN sequence of about 6 to about 10 nucleotides at a 3'-end of the first oligonucleotide.

In some examples, the first oligonucleotide is about 15 to about 25 nucleotides in length, such as about 18 to about 22 nucleotides in length or about 19 to about 21 nucleotides in length. In some examples, the first oligonucleotide is about 15, about 16, about 17, about 18, about 19 about 20, about 21, about 22, about 23, about 24 or about 25 nucleotides in length. In specific non-limiting examples, the first oligonucleotide is 20 nucleotides in length. In particular non-limiting examples, the first oligonucleotide comprises or consists of the nucleotide sequence CCTTGAAGGCGGACTGTGAG (SEQ ID NO: 1), CCTTGAAGGCGGACTGTGAG (SEQ ID NO: 3), GTCGGTGTCACTCTACTGCC (SEQ ID NO: 5), CGATCCGACAACACACGCTG (SEQ ID NO: 7), AGTCTCGTCGTAGGCTGCTG (SEQ ID NO: 9), CTACACATAGGCGTCCCGTG (SEQ ID NO: 11), ATCTACGAGCCGTCTGTGTC (SEQ ID NO: 13) or CTACACATCAACACACGCTG (SEQ ID NO: 15).

In some examples, the first oligonucleotide is a hot-start oligo that is activated at higher temperatures, such temperatures used for denaturation (e.g., 95° C.). In specific examples, the first oligonucleotide comprises a thermolabile phosphotriester modification at the 3' terminal internucleotide linkage and/or at the 3' penultimate internucleotide linkage.

In some examples, the second oligonucleotide is about 21 to about 35 nucleotides in length, such as about 24 to about 32 nucleotides in length, about 25 to about 31, or about 26 to about 29 nucleotides in length. In some examples, the first oligonucleotide is about 21, about 22, about 23, about 24, about 25 about 26, about 27, about 28, about 29, about 30, about 31, about 32, about 33, about 34 or about 35 nucleotides in length. In specific non-limiting examples, the second oligonucleotide is 28 nucleotides in length. In one example, the second oligonucleotide comprises or consists of the nucleotide sequence CCTTGAAGGCGGACTGTGAG-NNNNNNNN (SEQ ID NO: 2), CCTTGAAGGCGGACTGTGAGNNNNNN (SEQ ID NO: 4), GTCGGTGTCACTCTACTGCCNNNNNNNN (SEQ ID NO: 6), CGATCCGACAACACACGCTGNNNNNNNN (SEQ ID NO: 8), AGTCTCGTCGTAGGCTGCTGNNNNNNNN (SEQ ID NO: 10), CTACACATAGGCGTCCCGTGNNNNNNNN (SEQ ID NO: 12), ATCTACGAGCCGTCTGTGTCNNNNNNNN (SEQ ID NO: 14), or CTACACATCAACACACGCTGNNNNNNN (SEQ ID NO: 16).

In some embodiments, the kit further includes one or more of a reverse transcriptase, a thermostable DNA polymerase lacking 5' to 3' proofreading exonuclease activity, a PCR polymerase (such as a hot-start PCR polymerase), dNTPs and reaction buffer.

In some examples, the kit includes a first oligonucleotide and a second oligonucleotide respectively comprising or consisting of SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; or SEQ ID NO: 15 and SEQ ID NO: 16.

In specific examples, the kit includes a first oligonucleotide having the sequence of CCTTGAAGGCGGACTGTGAG (SEQ ID NO: 1), a second oligonucleotide having the sequence of CCTTGAAGGCGGACTGTGAG-NNNNNNNN (SEQ ID NO: 2), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of CCTTGAAGGCGGACTGTGAG (SEQ ID NO: 3), a second oligonucleotide having the sequence of CCTTGAAGGCGGACTGTGAGNNNNNN (SEQ ID NO: 4), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of GTCGGTGTCACTCTACTGCC (SEQ ID NO: 5), a second oligonucleotide having the sequence of GTCGGTGTCACTCTACTGCCNNNNNNNN (SEQ ID NO: 6), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of CGATCCGACAACACACGCTG (SEQ ID NO: 7), a second oligonucleotide having the sequence of CGATCCGACAACACACGCTGNNNNNNNN (SEQ ID NO: 8), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of AGTCTCGTCGTAGGCTGCTG (SEQ ID NO: 9), a second oligonucleotide having the sequence of AGTCTCGTCGTAGGCTGCTGNNNNNNNN (SEQ ID NO: 10), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of CTACACATAGGCGTCCCGTG (SEQ ID NO: 11), a second oligonucleotide having the sequence of CTACACATAGGCGTCCCGTGNNNNNNNN (SEQ ID NO: 12), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of ATCTACGAGCCGTCTGTGTC (SEQ ID NO: 13), a second oligonucleotide having the sequence of ATCTACGAGCCGTCTGTGTCNNNNNNNN (SEQ ID NO: 14), a reverse transcriptase, a thermostable DNA polymerase lacking 5' to 3' proofreading exonuclease activity, a PCR polymerase (such as a hot-start PCR polymerase), dNTPs and reaction buffer.

In other specific examples, the kit includes a first oligonucleotide having the sequence of CTACACATCAACACACGCTG (SEQ ID NO: 15), a second oligonucleotide having the sequence of CTACACATCAACACACGCTGNNNNNNNN (SEQ ID NO: 16), a reverse transcriptase, a thermostable DNA polymerase lacking 5' to 3' proofreading exonuclease activity, a PCR polymerase (such as a hot-start PCR polymerase), dNTPs and reaction buffer.

The kits can also contain one or more containers for the amplification, such as PCR tubes, and/or microwell plate(s) (such as 96- or 384-well plate(s)). In some examples the container is made of plastic. The kits can also contain instructions.

IV. Random Nucleic Acid Amplification for Sequencing

Figure 4A:
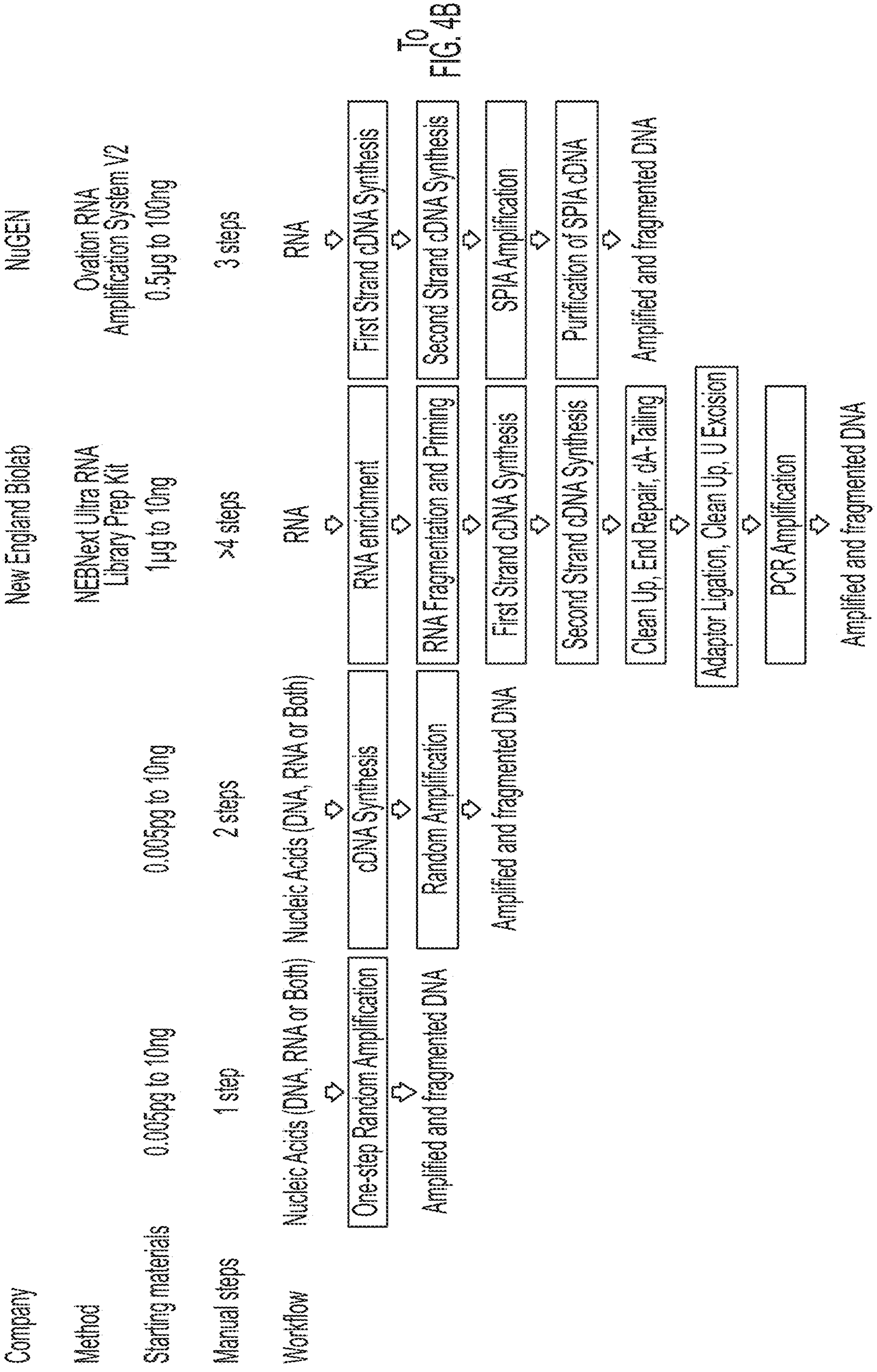
FIGS. 4A-4B show a schematic comparing the starting materials and manual steps of the low input, one-step and two-step amplification methods disclosed herein with four commercially available kits.
Figure 4B:
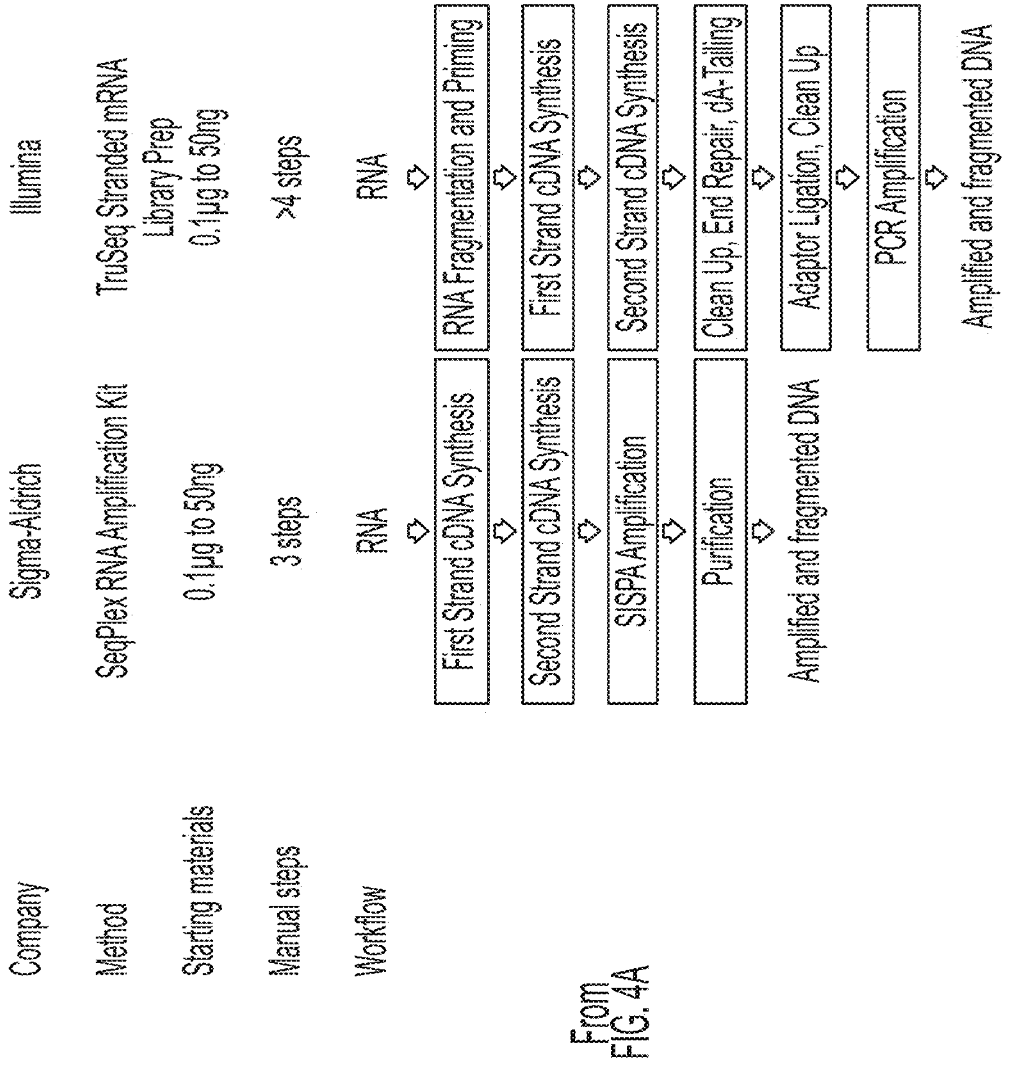

Nucleic acids from viruses and other microbes occur in minute amounts in the majority of biological samples. However, library construction and genome sequencing on the most common next-generation sequencing (NGS) platforms, such as Illumina (MISEQ™, HISEQ™, NEXTSEQ™ and NOVASEQ™), ION TORRENT™ PGM and NANOPORE™ Minion, require a considerable amount of extracted specimen nucleic acid, ranging from 0.1 ng to 10 µg (FIGS. 4A-4B). Nucleic acids from viral or other pathogens in blood, respiratory secretions, cerebrospinal fluid, fine needle aspirates, stool and other clinical specimens are often present at less than 0.001 ng in the extracted total nucleic acid. This poses considerable challenges for sequencing and identification of microorganisms directly from biological and clinical samples, without the use of culture techniques.

The present disclosure describes a one-step, single-tube method, and a two-step double-tube method, that allow random amplification (whole genome amplification) from extremely low starting quantities of nucleic acids, resulting in ample amounts of DNA for NGS or other molecular experiments. As compared to PCR, which amplifies a single target, a random amplification allows nonbiased universal amplification of all nucleic acid in a sample; this eliminates the need for microorganism-specific primer design and allows amplification of unknown microorganisms without prior sequence knowledge.

The one-step, single tube aspect of the disclosed method allows for minimum hands-on time as the user only needs to introduce input nucleic acid into a single reaction tube, and run it using a standard PCR machine for 2-3 hours. To achieve a one-step approach, this method uses the combination of (1) a reverse transcriptase (RT) for $1^{st}$ strand complementary DNA (cDNA) synthesis; (2) a thermostable DNA polymerase that lacks 5' →3' proofreading exonuclease activity (Exo-) for $2^{nd}$ strand synthesis; and (3) a hot-start PCR polymerase, which is only heat-activated in the third stage, to perform random PCR amplification.

The two-step method is also rapid and requires minimal hands-on manipulation. For RNA only or DNA/RNA input, the two-step approach combines a RT for $1^{st}$ strand complementary DNA (cDNA) synthesis; and a thermostable DNA polymerase that lacks 5'→3' proofreading exonuclease activity (Exo-) for $2^{nd}$ strand synthesis in a first step; and a PCR polymerase to perform random PCR amplification as the second step. For DNA only input, the two-step approach combines a thermostable DNA polymerase that lacks 5' →3' proofreading exonuclease activity (Exo-) for $1^{st}$ and $2^{nd}$ strand synthesis in a first step; and a PCR polymerase to perform random PCR amplification as the second step.

For both the one-step and two-step methods, the thermostability of the DNA polymerase allows for retention of its enzymatic activity during primer denaturation at 95° C. before $2^{nd}$ strand synthesis. Heat-activation of the hot-start PCR polymerase is achieved via appropriate thermocycling conditions.

As shown in FIGS. 1-3 and 5, the methods disclosed herein can be used to amplify DNA and/or RNA from biological samples (such as clinical samples) and involves the use of the following components in a single tube (for the one-step method) or two tubes (for the two-step method):

1. A reverse transcriptase (RT) or DNA polymerase for $1^{st}$ strand cDNA synthesis;
2. A thermostable DNA polymerase that lacks 5' to 3' proofreading exonuclease activity (Exo-polymerase) for second strand DNA synthesis;
3. A hot-start PCR polymerase for random PCR amplification (for the two-step method, the PCR polymerase does not need to be a hot-start polymerase);
4. Input nucleic acid (such as from a biological sample);
5. An oligo having a sequence that is not found in the species from which the biological sample was taken;
6. An oligo-polyN (having the same sequence as the oligo and a polyN sequence at the 3' end);
7. dNTPs; and
8. Reaction buffer One embodiment of the disclosed method is depicted in FIG. 1, with steps labelled A to G. This embodiments allows for amplification of DNA, RNA or a combination thereof. Only the initial set-up (step A) requires manual input from the user. (A) In a single tube, input nucleic acid (DNA, RNA or both) is introduced (for example, pipetted) into the reagent mix, which is freshly-mixed or premixed with the following components: Oligo, Oligo-polyN, $1^{st}$ strand RT (polymerase), $2^{nd}$ strand thermostable DNA polymerase Exo-, hot-start PCR polymerase, dNTPs and reaction buffer. A denaturation step at 75° C. is optional. In some examples, Oligo-polyN has the nucleotide sequence (N=random mixed base):

(SEQ ID NO: 2)
CCTTGAAGGCGGACTGTGAGNNNNNNNN (SEQ ID NO: 4)
CCTTGAAGGCGGACTGTGAGNNNNNN;

(SEQ ID NO: 6)
GTCGGTGTCACTCTACTGCCNNNNNNNN;

(SEQ ID NO: 8)
CGATCCGACAACACACGCTGNNNNNNNN;

(SEQ ID NO: 10)
AGTCTCGTCGTAGGCTGCTGNNNNNNNN;

(SEQ ID NO: 12)
CTACACATAGGCGTCCCGTGNNNNNNNN;

(SEQ ID NO: 14)
ATCTACGAGCCGTCTGTGTCNNNNNNNN;
or (SEQ ID NO: 16)
CTACACATCAACACACGCTGNNNNNNNN.

In some examples, the Oligo has the nucleotide sequence:

(SEQ ID NO: 1)
CCTTGAAGGCGGACTGTGAG;

(SEQ ID NO: 3)
CCTTGAAGGCGGACTGTGAG;

(SEQ ID NO: 5)
GTCGGTGTCACTCTACTGCC;

(SEQ ID NO: 7)
CGATCCGACAACACACGCTG;

(SEQ ID NO: 9)
AGTCTCGTCGTAGGCTGCTG;

(SEQ ID NO: 11)
CTACACATAGGCGTCCCGTG;

(SEQ ID NO: 13)
ATCTACGAGCCGTCTGTGTC;
or (SEQ ID NO: 15)
CTACACATCAACACACGCTG.

After introducing all components into a single tube (such as a PCR tube made of plastic), the remaining steps are performed in a standard automated thermocycler. (B) Oligo-polyN anneals to the input nucleic acid at random locations and the RT enzyme or polymerase carries out $1^{st}$ strand cDNA synthesis (C), producing random single-stranded cDNA with a primer overhang sequence. (D) A denaturation step (for example at 95° C.) inactivates the RT and denatures the first product. The reaction is cooled (for example to 4° C.) for oligo-polyN annealing on the newly synthesized first strand cDNA. (E) Second strand cDNA is generated using a thermostable Exo-DNA polymerase. (F) Following second strand synthesis, the double-stranded nucleic acid is denatured (for example at 95° C.), leading to activation of the hot-start DNA polymerase. (G) Random PCR is carried out by the hot-start PCR polymerase using the oligo as a primer and the second strand product as the template. In some examples, PCR is carried out for about 20 cycles to about 45 cycles, such as about 20, about 25, about 30, about 35, about 40 or about 45 cycles. A 35-cycle protocol can result in 34 billion-fold amplification.

Figure 2:
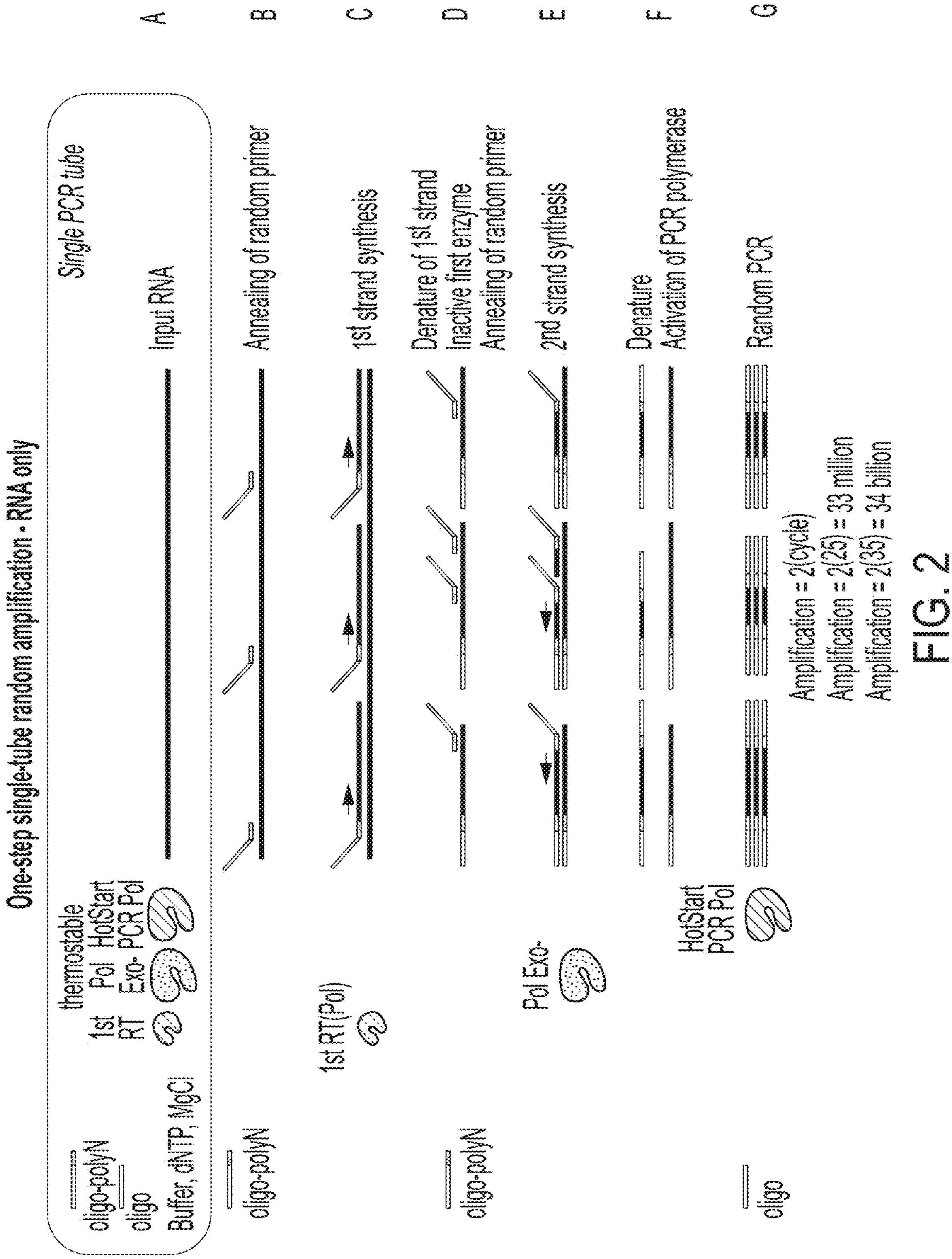
FIG. 2 is a schematic of a one-step, single tube, random nucleic acid amplification method using only RNA as the input. The illustrated method is a modification of the method shown in FIG. 1. Oligo, a primer such as CCTTGAAGGCGGACTGTGAG (SEQ ID NO: 1); Oligo-polyN, a primer with random mixed bases at the 3' end such as CCTTGAAGGCGGACTGTGAGNNNNNNNN (SEQ ID NO: 2); dNTP, deoxynucleotide; MgCl, magnesium chloride; $1^{st}$ RT (Pol), a reverse transcriptase for $1^{st}$ strand complementary DNA (cDNA) synthesis; Pol Exo-, a thermostable DNA polymerase that lacks 5' to 3' proofreading exonuclease activity for $2^{nd}$ strand synthesis; HotStart PCR Pol, a hot-start PCR polymerase that is only activated in the third stage to perform random PCR amplification.

Another embodiment of the disclosed method is depicted in FIG. 2, with steps labelled A to G. This embodiments allows for amplification of RNA only. (A) In a single tube, input RNA is introduced into the reagent mix, which is freshly-mixed or premixed with the following components: Oligo, Oligo-polyN, $1^{st}$ strand RT, $2^{nd}$ strand thermostable DNA polymerase Exo-, hot-start PCR polymerase, dNTPs and reaction buffer. A denaturation step at 75° C. is optional. In some examples, Oligo-polyN has the nucleotide sequence CCTTGAAGGCGGACTGTGAGNNNNNNNN (N=random mixed base; SEQ ID NO: 2). In some examples, the Oligo has the nucleotide sequence CCTT-GAAGGCGGACTGTGAG (SEQ ID NO: 1). In other examples, the Oligo and the Oligo-polyN are respectively SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; or SEQ ID NO: 15 and SEQ ID NO: 16.

After introducing all components into a single tube (such as a PCR tube made of plastic), the remaining steps are performed in a standard automated thermocycler. (B) Oligo-polyN anneals to the input RNA at random locations and the RT enzyme carries out $1^{st}$ strand cDNA synthesis (C), producing random single-stranded cDNA with a primer overhang sequence. (D) A denaturation step (for example at 95° C.) inactivates the RT and denatures the first product. The reaction is cooled (for example to 4° C.) for oligo-polyN annealing on the newly synthesized first strand cDNA. (E) Second strand cDNA is generated using a thermostable Exo-DNA polymerase. (F) Following second strand synthesis, the double-stranded nucleic acid is denatured (for example at 95° C.), leading to activation of the hot-start DNA polymerase. (G) Random PCR is carried out by the hot-start PCR polymerase using the oligo as a primer and the second strand product as the template. A 35-cycle protocol can result in 34 billion-fold amplification.

Yet another embodiment of the disclosed method is depicted in FIG. 3, with steps labelled A to G. This embodiments allows for amplification of input DNA only. (A) In a single tube (such as a PCR tube made of plastic), input DNA is introduced into the reagent mix, which is freshly-mixed or premixed with the following components: Oligo, Oligo-polyN, thermostable DNA polymerase Exo-(for $1^{st}$ and $2^{nd}$ strand DNA synthesis), hot-start PCR polymerase, dNTPs and reaction buffer. A denaturation step at 75° C. is optional. In some examples, Oligo-polyN has the nucleotide sequence CCTTGAAGGCGGACTGTGAGNNNNNNNN (N=random mixed base; SEQ ID NO: 2). In some examples, the Oligo has the nucleotide sequence CCTT-GAAGGCGGACTGTGAG (SEQ ID NO: 1). In other examples, the Oligo and the Oligo-polyN are respectively SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; or SEQ ID NO: 15 and SEQ ID NO: 16.

After introducing all components into a single tube (such as a PCR tube made of plastic), the remaining steps are performed in a standard automated thermocycler. (B) Oligo-polyN anneals to the input DNA at random locations and the Exo-polymerase carries out $1^{st}$ strand cDNA synthesis (C), producing random single-stranded cDNA with a primer overhang sequence. (D) A denaturation step (for example at 95° C.) denatures the first product. The reaction is cooled (for example to 4° C.) for oligo-polyN annealing on the newly synthesized first strand cDNA. (E) Second strand cDNA is generated using the thermostable Exo-DNA polymerase. (F) Following second strand synthesis, the double-stranded nucleic acid is denatured (for example at 95° C.), leading to activation of the hot-start DNA polymerase. (G) Random PCR is carried out by the hot-start PCR polymerase using the oligo as a primer and the second strand product as the template. A 35-cycle protocol can result in 34 billion-fold amplification.

The present disclosure further describes a two-step method that allows for random amplification (whole genome amplification) from extremely low starting quantities of nucleic acids, resulting in ample amounts of DNA for NGS or other molecular experiments. This embodiment is depicted in FIG. 5, with steps labelled A to G. (A) In a first tube (such as a first PCR tube made of plastic), input nucleic acid (DNA, RNA or both) is introduced (for example, pipetted) into the reagent mix, which is freshly-mixed or premixed with the following components: Oligo-polyN, $1^{st}$ strand RT (polymerase), 2nd strand thermostable DNA polymerase Exo-, dNTPs and reaction buffer. A denaturation step at 75° C. is optional. In some examples, Oligo-polyN has the nucleotide sequence CCTTGAAGGCGGACTGTGAGNNNNNNNNN (N=random mixed base; SEQ ID NO: 2). In other examples, the Oligo-polyN has the nucleotide sequence of SEQ ID NO: 4, SEQ ID NO: 6, SEQ ID NO: 8, SEQ ID NO: 10, SEQ ID NO: 12, SEQ ID NO: 14 or SEQ ID NO: 16.

After introducing these components into the first tube, the following steps are performed in a standard automated thermocycler. Oligo-polyN anneals (B) to the input nucleic acid at random locations and the RT enzyme or polymerase carries out $1^{st}$ strand cDNA synthesis (C), producing random single-stranded cDNA with a primer overhang sequence. (D) A denaturation step (for example at 95° C.) inactivates the RT and denatures the first product. The reaction is cooled (for example to 4° C.) for oligo-polyN annealing on the newly synthesized first strand cDNA. (E) Second strand cDNA is generated using a thermostable Exo-DNA polymerase. (F) Following second strand synthesis, the $2^{nd}$ strand synthesis product is transferred (e.g., pipetted) to a second tube (such as a second PCR tube made of plastic) containing Oligo and a PCR polymerase. The double-stranded nucleic acid is denatured (for example at 95° C.), leading to activation of the PCR polymerase. (G) Random PCR is carried out by the PCR polymerase using the oligo as a primer and the second strand product as the template. In some examples, the Oligo has the nucleotide sequence CCTTGAAGGCGGACTGTGAG (SEQ ID NO: 1). In other examples, the Oligo has the nucleotide sequence of SEQ ID NO: 3, SEQ ID NO: 5, SEQ ID NO: 7, SEQ ID NO: 9, SEQ ID NO: 11, SEQ ID NO: 13 or SEQ ID NO: 15. In some examples, PCR is carried out for about 20 cycles to about 45 cycles, such as about 20, about 25, about 30, about 35, about 40 or about 45 cycles. A 35-cycle protocol can result in 34 billion-fold amplification.

Also provided is a second two-step method that allows for random amplification from extremely low starting quantities of DNA only, resulting in ample amounts of amplified DNA for NGS or other molecular experiments. This embodiment is depicted in FIG. 6, with steps labelled A to G. (A) In a first tube (such as a first PCR tube made of plastic), input DNA is introduced (for example, pipetted) into the reagent mix, which is freshly-mixed or premixed with the following components: Oligo-polyN, thermostable DNA polymerase Exo-(for $1^{st}$ and $2^{nd}$ strand DNA synthesis), dNTPs and reaction buffer. A denaturation step at 75° C. is optional. In some examples, Oligo-polyN has the nucleotide sequence CCTTGAAGGCGGACTGTGAGNNNNNNNNN (N=random mixed base; SEQ ID NO: 2). In other examples, the Oligo-polyN has the nucleotide sequence of SEQ ID NO: 4, SEQ ID NO: 6, SEQ ID NO: 8, SEQ ID NO: 10, SEQ ID NO: 12, SEQ ID NO: 14 or SEQ ID NO: 16.

After introducing these components into the first tube, the following steps are performed in a standard automated thermocycler. Oligo-polyN anneals (B) to the input DNA at random locations and the polymerase carries out $1^{st}$ strand cDNA synthesis (C), producing random single-stranded cDNA with a primer overhang sequence. (D) A denaturation step (for example at 95° C.) denatures the first product. The reaction is cooled (for example to 4° C.) for oligo-polyN annealing on the newly synthesized first strand cDNA. (E) Second strand cDNA is generated using the thermostable Exo-DNA polymerase. (F) Following second strand synthesis, the 2nd strand synthesis product is transferred (e.g., pipetted) to a second tube (such as a second PCR tube made of plastic) containing Oligo and a PCR polymerase. The double-stranded nucleic acid is denatured (for example at 95° C.), leading to activation of the PCR polymerase. (G) Random PCR is carried out by the PCR polymerase using the oligo as a primer and the second strand product as the template. In some examples, the Oligo has the nucleotide sequence CCTTGAAGGCGGACTGTGAG (SEQ ID NO: 1). In other examples, the Oligo has the nucleotide sequence of SEQ ID NO: 3, SEQ ID NO: 5, SEQ ID NO: 7, SEQ ID NO: 9, SEQ ID NO: 11, SEQ ID NO: 13 or SEQ ID NO: 15. In some examples, PCR is carried out for about 20 cycles to about 45 cycles, such as about 20, about 25, about 30, about 35, about 40 or about 45 cycles. A 35-cycle protocol can result in 34 billion-fold amplification.

A review of current methodologies for random amplification, including whole genome and transcriptome amplification kits, demonstrated that these existing techniques require considerably higher amounts of input nucleic acid (FIGS. 4A-4B). In addition, other methodologies require at least three manual steps in the process, compared to the one-step and two-step procedures disclosed herein.

V. Exemplary Target Nucleic Acid

In some examples, the low input nucleic acid is nucleic acid from a pathogen or microbe, such as a viral, fungal, parasitic, protozoa or bacterial organism. However, the low input nucleic acid can be from any type of sample with low input target nucleic acid (such as a particular type of RNA transcript).

In some examples, the low input nucleic acid is from a target bacteria (for example, target bacteria nucleic acid molecule). Bacteria are prokaryotic organisms that in some examples cause disease (pathogenic bacteria). Bacteria can be classified based on the structural characteristics of their cell walls (Gram-positive or Gram-negative). Examples of target bacteria whose nucleic acids can be detected with the disclosed methods, include without limitation: *Acinetobacter baumanii, Actinobacillus* sp., Actinomycetes, *Actinomyces* sp. (such as *Actinomyces israelii* and *Actinomyces naeslundii*), *Aeromonas* sp. (such as *Aeromonas hydrophila, Aeromonas veronii* biovar *sobria* (*Aeromonas sobria*), and *Aeromonas caviae*), *Anaplasma phagocytophilum, Alcaligenes xylosoxidans, Acinetobacter baumanii, Actinobacillus actinomycetemcomitans, Bacillus* sp. (such as *Bacillus anthracia, Bacillus cereus, Bacillus subtilis, Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis*, and *Bordetella bronchiseptica*),

*Borrelia* sp. (such as *Borrelia recurrentis*, and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium* diphtherias, *Corynebacterium* jeikeum and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium intracellulare, Mycobacterium avium, Mycobacterium bovis*, and *Mycobacterium marinum*), *Mycoplasm* sp. (such as *Mycoplasma pneumoniae, Mycoplasma hominis*, and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia* tsutsugamushi) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equismilis*, Group D streptococci, *Streptococcus bovis*, Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio fumisii*), *Yersinia* sp. (such as *Yersinia enterocolitica, Yersinia pestis*, and *Yersinia pseudotuberculosis*) and *Xanthomonas maltophilia* among others.

In some embodiments, the low input nucleic acid is from a target virus (for example, target viral nucleic acid molecule). Viruses include positive-strand RNA viruses, negative-strand RNA viruses, DNA viruses and retroviruses. In some examples, the virus is from one of the following genera (family): Dependovirus (Parvoviridae), Kobuvirus (Picornaviridae), Lyssavirus (Rhabdoviridae), Polyomavirus (Polyomaviridae), Seadornavirus (Reoviridae), Alphavirus (Togaviridae), Orthobunyavirus (Bunyaviridae), Orthobunyavirus (Bunyaviridae), Orthobunyavirus (Bunyaviridae), Lymphocryptovirus (Herpesviridae), Vesiculovirus (Rhabdoviridae), Alphavirus (Togaviridae), Cosavirus (Picornaviridae), Orthopoxvirus (Poxviridae), Enterovirus (Picornaviridae), Nairovirus (Bunyaviridae), Flavivirus (Flaviviridae), Thogotovirus (Orthomyxoviridae), Nairovirus (Bunyaviridae), Lyssavirus (Rhabdoviridae), Alphavirus (Togaviridae), Ebolavirus (Filoviridae), Enterovirus (Picornaviridae), Cardiovirus (Picornaviridae), Lymphocryptovirus (Herpesviridae), Lyssavirus (Rhabdovirus), Pegivirus (Flaviviridae), Hantavirus (Bunyaviridae), Henipavirus (paramyxoviridae), Hepatovirus (picornaviridae), Orthohepadnavirus (Hepadnaviridae), Hepacivirus (Flaviviridae), Hepevirus (Unassigned), Deltavirus (Unassigned), Orthopoxvirus (Poxviridae), Mastadenovirus (Adenoviridae), Mamastrovirus (Astroviridae), Alphacoronavirus (Coronaviridae), Cytomegalovirus (Herpesviridae), Enterovirus (Picornaviridae), Simplexvirus (Herpesviridae), Simplexvirus (Herpesviridae), Roseolovirus (Herpesviridae), Roseolovirus (Herpesviridae), Rhadinovirus (Herpesviridae), Lentivirus (Retroviridae), Mupapillomavirus (Papillomaviridae), Alphapapillomavirus (Papillomaviridae), Alphapapillomavirus (Papillomaviridae), Respirovirus (Paramyxoviridae), Erythrovirus (Parvoviridae), Pneumovirus (Pneumoviridae), Enterovirus (Picornaviridae), Betacoronavirus (Coronaviridae), Spumavirus (Retroviridae), Deltaretrovirus (Retroviridae), Torovirus (Coronaviridae), Influenzavirus A (Orthomyxoviridae), Influenzavirus B (Orthomyxoviridae), Influenzavirus C (Orthomyxoviridae), Vesiculovirus (Rhabdoviridae), Polyomavirus (Polyomaviridae), Flavivirus (Flaviviridae), Arenavirus (Arenaviridae), Polyomavirus (Polyomaviridae), Flavivirus (Flaviviridae), Lyssavirus (Rhabdoviridae), Marburgvirus (Filoviridae), Flavivirus (Flaviviridae), Arenavirus (Arenaviridae), Norovirus (Caliciviridae), Flavivirus (Flaviviridae), Arenavirus (Arenaviridae), Arenavirus (Arenaviridae), Alphavirus (Togaviridae), Betacoronavirus (Coronaviridae), Morbilivirus (Paramyxoviridae), Cardiovirus (Picornaviridae), Polyomavirus (Polyomaviridae), Lyssavirus (Rhabdoviridae), Molluscipoxvirus (Poxviridae), Orthopoxvirus (Poxviridae), Rubulavirus (Paramyxoviridae), Flavivirus (Flaviviridae), Hantavirus (Bunyavirus), Henipavirus (Paramyxoviridae), Norovirus (Caliciviridae), Alphavirus (Togaviridae), Parapoxvirus (Poxviridae), Orthobunyavirus (Bunyaviridae), Arenavirus (Arenaviridae), Enterovirus (Picornaviridae), Phlebovirus (Bunyaviridae), Hantavirus (Bunyavirus), Lyssavirus (Rhabdoviridae), Phlebovirus (Bunyaviridae), Rosavirus (Picornaviridae), Alphavirus (Togaviridae), Rotavirus (Reoviridae), Rotavirus (Reoviridae), Rotavirus (Reoviridae), Rubivirus (Togaviridae), Alphavirus (Togaviridae), Salivirus (Picornaviridae), Phlebovirus (Bunyaviridae), Sapovirus (Caliciviridae), Alphavirus (Togaviridae), Hantavirus (Bunyavirus), Spumavirus (Retroviridae), Rubulavirus (Paramyxoviridae), Alphavirus (Togaviridae), Norovirus (Caliciviridae), Flavivirus (Flaviviridae), Flavivirus (Flaviviridae), Alphatorquevirus (Anelloviridae), Phlebovirus (Bunyaviridae), Phlebovirus (Bunyaviridae), Orthopoxvirus (Poxviridae), Varicellovirus (Herpesviridae), Orthopoxvirus (Poxviridae), Alphavirus (Togaviridae), Vesiculovirus (Rhabdoviridae), Alphavirus (Togaviridae), Polyomavirus (Polyomaviridae), Flavivirus (Flaviviridae), Orthopoxvirus (Poxviridae), Orthopoxvirus (Poxviridae), Flavivirus (Flaviviridae), and Flavivirus (Flaviviridae). In specific examples, the virus is an Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16,18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, Semliki forest virus, Seoul virus, Simian foamy virus, Simian virus 5, Sindbis virus, Southampton virus, St. louis encephalitis virus, Tick-borne powassan virus, Torque teno virus, Toscana virus, Uukuniemi virus, Vaccinia virus, Varicella-zoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, or Zika virus.

In some examples, the low input nucleic acid is a target protozoa, nematode, or fungi (for example, target protozoa, nematode, or fungal nucleic acid molecule). Exemplary protozoa include, but are not limited to, *Plasmodium* (e.g., *Plasmodium falciparum* to diagnose malaria), *Leishmania, Acanthamoeba, Giardia, Entamoeba, Cryptosporidium, Isospora, Balantidium, Trichomonas, Trypanosoma* (e.g., *Trypanosoma brucei*), *Naegleria*, and *Toxoplasma*. Exemplary fungi include, but are not limited to, *Aspergillus* sp. (including *Aspergillus fumigatus*), *Candida* sp., (such as *Candida albicans*), *C. neoformans, C. gattii, Coccidioides* sp., *Coccidiodes immitis, Trichophyton* sp., *Microsporum* sp., *Epidermophyton* sp., Tinea sp., and *Blastomyces dermatitidis.*

In some examples, the low input nucleic acid is from a tumor sample, such as a cancer sample (e.g., fine needle aspirate or other sample that includes tumor cells). In some examples, the low input nucleic acid is present in a solid tumor sample, such as breast carcinomas (e.g. lobular and duct carcinomas, such as a triple negative breast cancer), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, head and neck squamous cell carcinoma, or a lymphatic tumor (including B-cell and T-cell malignant lymphoma). In one example, low input nucleic acid is present in an adenocarcinoma sample. In one example, low input nucleic acid is present in a liquid tumor sample, such as one from a lymphatic, white blood cell, or other type of leukemia. For example, the low input nucleic acid can be present in a blood cancer sample, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), a lymphoma (such as Hodgkin's lymphoma or non-Hodgkin's lymphoma), or a myeloma.

The following examples are provided to illustrate certain particular features and/or embodiments. These examples should not be construed to limit the disclosure to the particular features or embodiments described.

EXAMPLES

Example 1: Detection of Viral RNA by One-Step Random Nucleic Acid Amplification This example describes amplification of RNA from two different viruses using the single tube/container, one-step random amplification method disclosed herein.

Serial dilutions of transcript RNA from Enterovirus D68 and Cosavirus were prepared and tested in the one-step amplification assay to determine the limit of detection. Enterovirus D68 transcript length was 1100 bp, and Cosavirus transcript length was 488 bp. A reaction master mix was prepared in sterile PCR tubes. The reaction master mix included reaction buffer, oligo (SEQ ID NO: 1), oligo-polyN (SEQ ID NO: 2), reverse transcriptase (SuperScript IV Reverse Transcriptase, Thermo Fisher Scientific), thermostable DNA polymerase Exo-(Vent® (exo-) DNA Polymerase, New England Biolabs), hot-start PCR polymerase (HotStarTaq DNA Polymerase, QIAGEN), dNTPs, as well as reaction buffer, dithiothreitol (DTT) and RNAse inhibitor in the following volumes (in a single tube):

| Volume | Components (initial concentration) |
|---|---|
| 4 μl | Input (viral) DNA/RNA |
| 0.5 μl | dNTP (10 mM) |
| 0.5 μl | oligo (100 μM) |
| 0.5 μl | oligo-polyN (100 μM) |
| 2 μl | 5X Superscript SSIV Buffer |
| 0.5 μl | DTT (100 mM) |
| 0.5 μl | RNAse inhibitor (40 U/μL; Ribolock) |
| 0.5 μl | thermostable DNA polymerase Exo- (2 U/μL; Vent ® (exo-) DNA Polymerase) |
| 0.5 μl | hot-start PCR polymerase (5 U/μL; HotStarTaq DNA Polymerase) |
| 0.5 μl | Reverse Transcriptase (200 U/μL: Superscript IV) |
| 10 μl | (total volume) |

(A) Sample nucleic acid (4 μl) was added to reaction master mix for a total volume of 10 Samples were mixed by vortexing and subjected to thermocycling using the following parameters (see also FIG. 1):

(B) Annealing at 23° C. for 10 minutes. Oligo-polyN anneals to the input nucleic acid at random locations and the RT enzyme carries out $1^{st}$ strand cDNA synthesis.

(C) First strand synthesis at 52° C. for 10 minutes. This step produces random single-stranded cDNA with a primer overhang sequence.

(D) Denaturation at 95° C. for 1 minute. Denaturation inactivates the RT and denatures the first product. The reaction was cooled to 55° C. for 1 minutes, which allows for oligo-polyN annealing on the newly synthesized first strand cDNA.

(E) Second strand synthesis at 72° C. for 30 minutes. cDNA is generated by the thermostable Exo-DNA polymerase.

(F) Denaturation and hot-start activation at 95° C. for 15 minutes. This step denatures the double-stranded nucleic acid and activates the hot-start DNA polymerase.

(G) 35 cycles of PCR (35 cycles of 95° C. for 30 seconds; 59° C. for 30 seconds and 72° C. for 1 minute; followed by 72° C. for 3 minutes and hold at 4° C.). PCR is carried out by the hot-start PCR polymerase using the oligo as a primer and the second strand product as the template.

Amplified product was evaluated using next generation sequencing at the end of thermocycling. In this experiment, Nextera XT DNA Library Prep Kit and MISEQ™ v2 500 cycles were used for sequencing. The results are shown in Table 1.

TABLE 1

Lower Limits for Detection and Sequencing of Nucleic Acid

| Virus | Limit off detection (copy number) | Starting material equivalent | Limit of full sequencing (copy number) | Starting material equivalent |
|---|---|---|---|---|
| Enterovirus D68 | $10^4$ (0.017 attomole) | 0.005 pg | $10^6$ (1.7 attomole) | 0.5 pg |
| Cosavirus | $10^4$ (0.017 attomole) | 0.003 pg | $10^5$ (0.17 attomole) | 0.03 pg |

The lower limit of detection of input nucleic acid was about $10^4$ copies (~0.005 pg). To enable full sequencing of input nucleic acid, the lower limit was about $10^6$ copies (~0.5 pg). The results demonstrated that virus could be detected and some sequence could be obtained at a lower copy number (approximately $10^4$ copies), but to obtain full genome sequencing, greater copy numbers were needed (approximately $10^6$ copies). The resulting sequence was 100% identical for all dilutions of the same virus. These results further demonstrated that the one-step, single tube, random amplification method exceeded the limit of commercially available whole genome sequencing kits (see FIGS. 4A-4B), which require at least 10 ng of input nucleic acid.

To confirm that this method could be applied universally to a wide range of different viruses, additional studies were performed using a diverse set of viruses. Using the method described above, viral nucleic acid from enterovirus A24, enterovirus A71, parechovirus and norovirus was successfully amplified and subjected to whole genome sequencing.

Example 2: Comparison of Nucleic Acid Amplification Using the One-Step and Two-Step Methods This example describes a study to compare nucleic acid amplification of low input RNA between the one-step and two-step methods disclosed herein.

RNA was isolated from HeLa cells and serially diluted from 10 ng/μl to 1 pg/μl as follows: 10 ng/μl, 1 ng/μl, 100 μg/μl, 10 μg/μl, 1 μg/μl, 100 pg/μl, 10 pg/μl and 1 pg/μl. The one-step and two-step amplification methods were carried out as shown in FIG. 1 and FIG. 5, respectively, using 4 μl of RNA from each dilution as the input nucleic acid.

Figure 7:
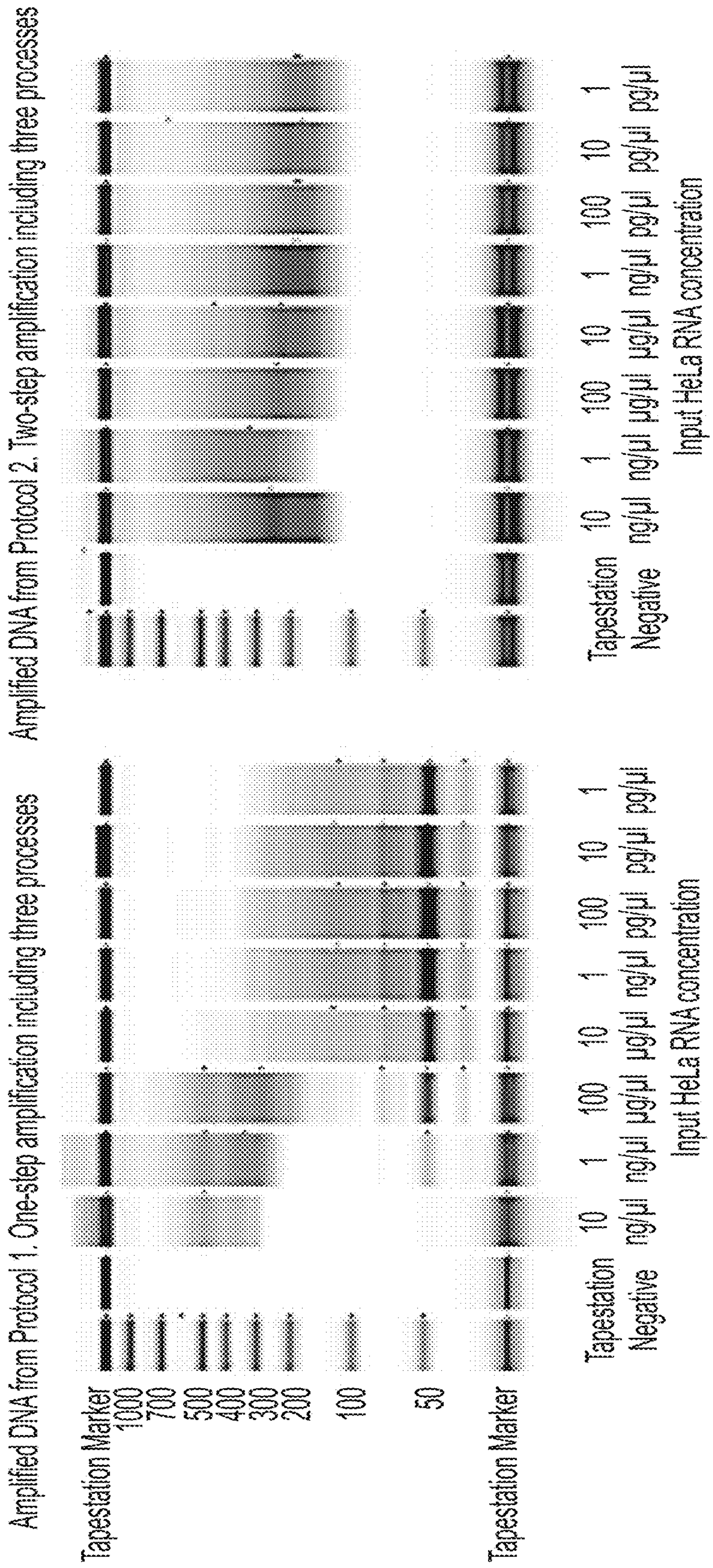
FIG. 7 shows amplification of HeLa cell RNA using either the one-step method (left) or the two-step method (right). HeLa RNA was serially diluted from 10 ng/μl to 1 pg/μl as follows: 10 ng/μl, 1 ng/μl, 100 μg/μl, 10 μg/μl, 1 μg/μl, 100 pg/μl, 10 pg/μl and 1 pg/μl. The methods were performed using 4 μl of RNA from each dilution as the input nucleic acid. The product of each amplification was evaluated by electrophoresis.

Amplification products from each dilution for the one-step and two-step methods were analyzed by electrophoresis. As shown in FIG. 7, the two-step method (right) resulted in an increase in the amplified DNA fragment size compared to the one-step method (left).

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method for random amplification of low input nucleic acid, comprising:

mixing in a single container a biological sample containing input nucleic acid, a reverse transcriptase, a thermostable DNA polymerase lacking 5' to 3' proofreading exonuclease activity, a hot-start polymerase chain reaction (PCR) polymerase, a first oligonucleotide, a second oligonucleotide, deoxynucleotide triphosphates (dNTPs) and reaction buffer, thereby generating a mixture, wherein the first oligonucleotide is 15 to 30 nucleotides in length and the second oligonucleotide consists of the first oligonucleotide with an additional polyN sequence of 6 to 10 nucleotides at a 3'-end of the first oligonucleotide; and subjecting the mixture to the following thermocycling steps:

an annealing step to permit annealing of the second oligonucleotide to the input nucleic acid;

a first synthesis step to permit the reverse transcriptase to generate first strand cDNA;

a denaturation step to denature the first strand cDNA from the input nucleic acid and to inactivate the reverse transcriptase;

a cooling step to permit annealing of the second oligonucleotide to the first strand cDNA;

a second synthesis step to permit the thermostable DNA polymerase to generate second strand cDNA;

a hot-start PCR polymerase activation step; and

PCR using the first oligonucleotide as primer and the second strand cDNA as template.

2. The method of claim 1, wherein the input nucleic acid comprises RNA.

3. The method of claim 1, wherein the input nucleic acid comprises DNA.

4. The method of claim 1, wherein the input nucleic acid comprises viral nucleic acid.

5. The method of claim 1, wherein the input nucleic acid comprises bacterial nucleic acid.

6. The method of claim 1, wherein the biological sample contains less than 10 pg input nucleic acid.

7. The method of claim 1, wherein the biological sample contains less than 1 pg input nucleic acid.

8. The method of claim 1, wherein the annealing step is performed at 23° C. to 52° C.

9. The method of claim 1, wherein the first synthesis step is performed at 40° C. to 60° C.

10. The method of claim 1, wherein the denaturation step is performed at 95° C.

11. The method of claim 1, wherein the cooling step is performed at 4° C. to 55° C.

12. The method of claim 1, wherein the second synthesis step is performed at 60° C. to 72° C.

13. The method of claim 1, wherein the hot-start polymerase activation step is performed at 95° C.

14. The method of claim 1, wherein the first oligonucleotide is 18 to 22 nucleotides in length.

15. The method of claim 1, wherein the first oligonucleotide is 20 nucleotides in length.

16. The method of claim 1, wherein the first oligonucleotide comprises or consists of the nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13 or SEQ ID NO: 15.

17. The method of claim 1, wherein the second oligonucleotide comprises or consists of the nucleotide sequence of SEQ ID NO: 2, SEQ ID NO: 4, SEQ ID NO: 6, SEQ ID NO: 8, SEQ ID NO: 10, SEQ ID NO: 12, SEQ ID NO: 14 or SEQ ID NO: 16.

18. The method of claim 1, wherein the first oligonucleotide comprises a thermolabile phosphotriester modification at the 3'-terminal internucleotide linkage.

19. The method of claim 18, wherein the first oligonucleotide further comprises a thermolabile phosphotriester modification at the 3'-penultimate internucleotide linkage.

20. A method for random amplification of low input nucleic acid, comprising:

(i) providing a first oligonucleotide and a second oligonucleotide, wherein the first oligonucleotide is 15 to 30 nucleotides in length and the second oligonucleotide consists of the first oligonucleotide with an additional polyN sequence of 6 to 10 nucleotides at a 3'-end of the first oligonucleotide;

(ii) mixing in a first container a biological sample containing input nucleic acid, a reverse transcriptase, a thermostable DNA polymerase lacking 5' to 3' proofreading exonuclease activity, the second oligonucleotide, deoxynucleotide triphosphates (dNTPs) and reaction buffer, thereby generating a first mixture;

(iii) subjecting the first mixture to the following thermocycling steps:

an annealing step to permit annealing of the second oligonucleotide to the input nucleic acid;

a first synthesis step to permit the reverse transcriptase to generate first strand cDNA;

a denaturation step to denature the first strand cDNA from the input nucleic acid and to inactivate the reverse transcriptase;

a cooling step to permit annealing of the second oligonucleotide to the first strand cDNA;

a second synthesis step to permit the thermostable DNA polymerase to generate second strand cDNA, thereby producing a second strand cDNA product;

(iv) mixing in a second container the second strand cDNA product, a polymerase chain reaction (PCR) polymerase, the first oligonucleotide, dNTPs and reaction buffer, thereby generating a second mixture; and (v) subjecting the second mixture to the following thermocycling steps:

a PCR polymerase activation step; and a PCR using the first oligonucleotide as primer and the second strand cDNA as template.

21. A method for random amplification of low input DNA, comprising:

mixing in a single container a biological sample containing input DNA, a thermostable DNA polymerase lacking 5' to 3' proofreading exonuclease activity, a hot-start polymerase chain reaction (PCR) polymerase, a first oligonucleotide, a second oligonucleotide, deoxynucleotide triphosphates (dNTPs) and reaction buffer, thereby generating a mixture, wherein the first oligonucleotide is 15 to 30 nucleotides in length and the second oligonucleotide consists of the first oligonucleotide with an additional polyN sequence of 6 to 10 nucleotides at a 3'-end of the first oligonucleotide; and subjecting the mixture to the following thermocycling steps:

an annealing step to permit annealing of the second oligonucleotide to the input DNA;

a first synthesis step to permit the thermostable DNA polymerase to generate first strand cDNA;

a denaturation step to denature the first strand cDNA from the input DNA;

a cooling step to permit annealing of the second oligonucleotide to the first strand cDNA;

a second synthesis step to permit the thermostable DNA polymerase to generate second strand cDNA;

a hot-start PCR polymerase activation step; and

PCR using the first oligonucleotide as primer and the second strand cDNA as template.

22. A method for random amplification of low input DNA, comprising:

(i) providing a first oligonucleotide and a second oligonucleotide, wherein the first oligonucleotide is 15 to 30 nucleotides in length and the second oligonucleotide consists of the first oligonucleotide with an additional polyN sequence of 6 to 10 nucleotides at a 3'-end of the first oligonucleotide;

(ii) mixing in a first container a biological sample containing input DNA, a thermostable DNA polymerase lacking 5' to 3' proofreading exonuclease activity, the second oligonucleotide, deoxynucleotide triphosphates (dNTPs) and reaction buffer, thereby generating a first mixture;

(iii) subjecting the first mixture to the following thermocycling steps:

an annealing step to permit annealing of the second oligonucleotide to the input DNA;

a first synthesis step to permit the thermostable DNA polymerase to generate first strand cDNA;

a denaturation step to denature the first strand cDNA from the input DNA;

a cooling step to permit annealing of the second oligonucleotide to the first strand cDNA;

a second synthesis step to permit the thermostable DNA polymerase to generate second strand cDNA, thereby producing a second strand cDNA product;

(iv) mixing in a second container the second strand cDNA product, a polymerase chain reaction (PCR) polymerase, the first oligonucleotide, dNTPs and reaction buffer, thereby generating a second mixture; and (v) subjecting the second mixture to the following thermocycling steps:

a PCR polymerase activation step; and a PCR using the first oligonucleotide as primer and the second strand cDNA as template.

23. A kit for random amplification of low input nucleic acid, comprising:

a first oligonucleotide and a second oligonucleotide, wherein the sequence of the first oligonucleotide and the sequence of the second oligonucleotide respectively consist of:

SEQ ID NO: 3 and SEQ ID NO: 4;

SEQ ID NO: 5 and SEQ ID NO: 6;

SEQ ID NO: 7 and SEQ ID NO: 8;

SEQ ID NO: 9 and SEQ ID NO: 10;

SEQ ID NO: 11 and SEQ ID NO: 12;

SEQ ID NO: 13 and SEQ ID NO: 14; or

SEQ ID NO: 15 and SEQ ID NO: 16; and a thermostable DNA polymerase lacking 5' to 3' and 3' to 5' proofreading exonuclease activity.

24. The kit of claim 23, further comprising one or more of a reverse transcriptase, a hot-start PCR polymerase, dNTPs, at least one container for performing random amplification, and reaction buffer.

25. The kit of claim 23, further comprising an oligonucleotide consisting of the sequence of SEQ ID NO: 1 and/or an oligonucleotide consisting of the sequence of SEQ ID NO: 2.

26. The kit of claim 23, wherein the first oligonucleotide comprises a thermolabile phosphotriester modification at the 3'-terminal internucleotide linkage.

27. The kit of claim 26, wherein the first oligonucleotide further comprises a thermolabile phosphotriester modification at the 3'-penultimate internucleotide linkage.

* * * * *

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1

ccttgaaggc ggactgtgag                                                  20


<210> SEQ ID NO 2
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 2

ccttgaaggc ggactgtgag nnnnnnnn                                         28


<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3

ccttgaaggc ggactgtgag                                                  20


<210> SEQ ID NO 4
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(26)
<223> OTHER INFORMATION: n is a, c, g, or t

<400> SEQUENCE: 4

ccttgaaggc ggactgtgag nnnnnn                                           26


<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5

gtcggtgtca ctctactgcc                                                  20


<210> SEQ ID NO 6
<211> LENGTH: 28
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 6

gtcggtgtca ctctactgcc nnnnnnnn                                      28


<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7

cgatccgaca acacacgctg                                               20


<210> SEQ ID NO 8
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 8

cgatccgaca acacacgctg nnnnnnnn                                      28


<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9

agtctcgtcg taggctgctg                                               20


<210> SEQ ID NO 10
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 10

agtctcgtcg taggctgctg nnnnnnnn                                      28


<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
```

-continued ctacacatag gcgtcccgtg 20

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 12
ctacacatag gcgtcccgtg nnnnnnnn 28

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
atctacgagc cgtctgtgtc 20

<210> SEQ ID NO 14
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(28)
<223> OTHER INFORMATION: n is a, c, g, or t

<400> SEQUENCE: 14
atctacgagc cgtctgtgtc nnnnnnnn 28

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ctacacatca acacacgctg 20

<210> SEQ ID NO 16
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (21)..(27)
<223> OTHER INFORMATION: n is a, c, g, or t

<400> SEQUENCE: 16
ctacacatca acacacgctg nnnnnnn 27